(12) United States Patent
Opalsky et al.

(10) Patent No.: US 10,488,353 B2
(45) Date of Patent: Nov. 26, 2019

(54) APPARATUS AND SYSTEM FOR PERFORMING THERMAL MELT ANALYSES AND AMPLIFICATIONS

(71) Applicant: GEN-PROBE INCORPORATED, San Diego, CA (US)

(72) Inventors: David Opalsky, San Diego, CA (US); Norbert D. Hagen, Carlsbad, CA (US); Rolf Silbert, Del Mar, CA (US); Sean S. Chiu, Redmond, WA (US); Haitao Li, San Diego, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 387 days.

(21) Appl. No.: 15/440,806

(22) Filed: Feb. 23, 2017

(65) Prior Publication Data

US 2017/0160218 A1 Jun. 8, 2017

Related U.S. Application Data

(62) Division of application No. 13/956,060, filed on Jul. 31, 2013, now Pat. No. 9,588,069.

(60) Provisional application No. 61/677,790, filed on Jul. 31, 2012.

(51) Int. Cl.
*B01L 7/00* (2006.01)
*G01N 25/04* (2006.01)
*G01N 21/64* (2006.01)
*B01L 9/06* (2006.01)

(52) U.S. Cl.
CPC ............ *G01N 25/04* (2013.01); *B01L 7/5255* (2013.01); *G01N 21/6428* (2013.01); *B01L 9/06* (2013.01); *B01L 2200/028* (2013.01); *B01L 2300/0627* (2013.01); *B01L 2300/1827* (2013.01); *G01N 2021/6432* (2013.01); *G01N 2021/6439* (2013.01)

(58) Field of Classification Search
None
See application file for complete search history.

(56) References Cited

U.S. PATENT DOCUMENTS

| | | | |
|---|---|---|---|
| 4,021,123 A | 5/1977 | Atwood et al. |
| 4,678,752 A | 7/1987 | Thorne et al. |
| 4,683,195 A | 7/1987 | Mullis et al. |
| 4,800,159 A | 1/1989 | Mullis et al. |
| 4,851,330 A | 7/1989 | Kohne |
| 4,902,624 A | 2/1990 | Columbus et al. |

(Continued)

FOREIGN PATENT DOCUMENTS

| | | |
|---|---|---|
| CA | 2549754 A1 | 12/2006 |
| CN | 102422163 A | 4/2012 |

(Continued)

OTHER PUBLICATIONS

Stratagene (Mx3000P™ Real-Time PCR System Instruction Manual, attached, Dec. 31, 2004).*

(Continued)

*Primary Examiner* — Aaron A Priest
(74) *Attorney, Agent, or Firm* — Charles B. Cappellari; Richard Wydeven

(57) ABSTRACT

The present disclosure provides apparatus, systems, and methods for conducting rapid, accurate, and consistent heated amplifications and/or thermal melt analyses.

31 Claims, 16 Drawing Sheets

(56) References Cited

U.S. PATENT DOCUMENTS

| | | |
|---|---|---|
| 4,683,202 B1 | 11/1990 | Mullis |
| 5,241,363 A | 8/1993 | Garner |
| 5,244,633 A | 9/1993 | Jakubowicz et al. |
| 5,354,663 A | 10/1994 | Charm et al. |
| 5,399,491 A | 3/1995 | Kacian et al. |
| 5,415,839 A | 5/1995 | Zaun et al. |
| 5,427,930 A | 6/1995 | Birkenmeyer et al. |
| 5,437,990 A | 8/1995 | Burg et al. |
| 5,482,384 A | 1/1996 | Lyle |
| 5,501,963 A | 3/1996 | Burckhardt |
| 5,541,308 A | 7/1996 | Hogan et al. |
| 5,554,516 A | 9/1996 | Kacian et al. |
| 5,578,270 A | 11/1996 | Reichler et al. |
| 5,612,200 A | 3/1997 | Dattagupta et al. |
| 5,686,272 A | 11/1997 | Marshall et al. |
| 5,736,106 A | 4/1998 | Ishiguro et al. |
| 5,779,981 A | 7/1998 | Danssaert et al. |
| 5,840,573 A | 11/1998 | Fields |
| 5,846,491 A | 12/1998 | Choperena et al. |
| 5,960,160 A | 9/1999 | Clark et al. |
| 5,985,672 A | 11/1999 | Kegelman et al. |
| 5,998,217 A | 12/1999 | Rao et al. |
| 6,068,978 A | 5/2000 | Zaun et al. |
| 6,086,827 A | 7/2000 | Horner et al. |
| 6,096,561 A | 8/2000 | Tayi |
| 6,197,520 B1 | 3/2001 | Wittwer et al. |
| 6,248,518 B1 | 6/2001 | Parkhurst et al. |
| 6,335,166 B1 | 1/2002 | Ammann et al. |
| 6,391,940 B1 | 5/2002 | Blackwell et al. |
| 6,448,066 B1 | 9/2002 | Wheatcroft |
| 6,472,156 B1 | 10/2002 | Wittwer et al. |
| 6,506,568 B2 | 1/2003 | Shriver et al. |
| 6,503,711 B1 | 4/2003 | Krull et al. |
| 6,558,947 B1 | 5/2003 | Lund et al. |
| 6,605,213 B1 | 8/2003 | Ammann et al. |
| 6,635,427 B2 | 10/2003 | Wittwer et al. |
| 6,664,064 B1 | 12/2003 | Dietmaier |
| 6,852,986 B1 | 2/2005 | Lee et al. |
| 7,019,267 B2 | 3/2006 | Weinfield et al. |
| 7,081,226 B1 | 7/2006 | Wittwer et al. |
| 7,109,495 B2 | 9/2006 | Lee et al. |
| 7,115,374 B2 | 10/2006 | Linnen |
| 7,160,998 B2 | 1/2007 | Wittwer et al. |
| 7,255,833 B2 | 8/2007 | Chang et al. |
| 7,282,333 B2 | 10/2007 | Brow et al. |
| 7,319,022 B1 | 1/2008 | Mahoney et al. |
| 7,327,459 B2 | 2/2008 | Kim et al. |
| 7,348,141 B2 | 3/2008 | French et al. |
| 7,374,885 B2 | 5/2008 | Becker et al. |
| 7,381,811 B2 | 6/2008 | Weisburg et al. |
| 7,419,786 B2 | 9/2008 | Kurane et al. |
| 7,456,281 B2 | 11/2008 | Dujols |
| 7,462,469 B2 | 12/2008 | Bass et al. |
| 7,466,908 B1 | 12/2008 | Lem et al. |
| 7,482,121 B2 | 1/2009 | Sorge et al. |
| 7,485,442 B2 | 2/2009 | Afonina et al. |
| 7,541,147 B2 | 6/2009 | Marshall et al. |
| 7,547,512 B2 | 6/2009 | Peiris et al. |
| 7,549,978 B2 | 6/2009 | Carlson et al. |
| 7,560,256 B2 | 7/2009 | Ammann et al. |
| 7,897,337 B2 | 3/2011 | Macioszek et al. |
| 7,932,081 B2 | 4/2011 | Lair et al. |
| 7,964,413 B2 | 6/2011 | Macioszek et al. |
| 9,588,069 B2 | 3/2017 | Opalsky et al. |
| 2004/0014119 A1 | 1/2004 | Itoh et al. |
| 2005/0092643 A1 | 5/2005 | Craven |
| 2005/0202491 A1 | 9/2005 | Nelson et al. |
| 2006/0127906 A1 | 6/2006 | Lee et al. |
| 2007/0148677 A1 | 6/2007 | Chagovetz et al. |
| 2007/0154922 A1 | 7/2007 | Collier et al. |
| 2007/0172836 A1 | 7/2007 | Exner et al. |
| 2007/0184453 A1 | 8/2007 | Sagner et al. |
| 2007/0196238 A1 | 8/2007 | Kennedy et al. |
| 2008/0000892 A1 | 1/2008 | Hirano et al. |
| 2008/0089818 A1 | 4/2008 | Ammann et al. |
| 2009/0029877 A1 | 1/2009 | Ammann et al. |
| 2009/0130745 A1 | 5/2009 | Williams et al. |
| 2009/0155808 A1 | 6/2009 | Hansen et al. |
| 2009/0218518 A1 | 9/2009 | Schirr et al. |
| 2010/0075312 A1 | 3/2010 | Davies et al. |
| 2010/0099581 A1 | 4/2010 | Arciniegas |
| 2010/0279276 A1 | 11/2010 | Kacian |
| 2010/0288395 A1 | 11/2010 | Hagen et al. |
| 2011/0236960 A1 | 9/2011 | Bird et al. |
| 2012/0221252 A1 | 8/2012 | Heinz et al. |

FOREIGN PATENT DOCUMENTS

| | | |
|---|---|---|
| DE | 4214866 C1 | 7/1993 |
| DE | 19964054 A1 | 7/2001 |
| DE | 102007057651 A1 | 6/2009 |
| EP | 0933132 A2 | 8/1999 |
| EP | 1686190 A1 | 8/2006 |
| JP | 5312813 | 11/1993 |
| JP | 2005010049 | 1/2005 |
| JP | 2002116202 | 4/2012 |
| WO | 8801302 A1 | 2/1988 |
| WO | 8810315 A1 | 12/1988 |
| WO | 9215853 A1 | 9/1992 |
| WO | 9913976 A1 | 3/1999 |
| WO | 0049557 A2 | 8/2000 |
| WO | 0173399 A2 | 10/2001 |
| WO | 2010/132885 A2 | 11/2010 |

OTHER PUBLICATIONS

Buchman et al., "Selective RNA Amplification: A Novel Method Using dUMP-containing Primers and Uracil DNA Glycosylase," PCR Methods and Applications, Aug. 1993, pp. 28-31, vol. 3, No. 1, Cold Spring Harbor Laboratory Press, Woodbury, NY, US.

Idaho Technology Inc., HR1™ High Resolution Melter, Technical Users Manual, Rev-01 (2003).

Imboden et al., "Simultaneous Detection of DNA and RNA by Differential Polymerase Chain Reaction (DIFF-PCR)", PCR Methods and Applications, Aug. 1993, pp. 23-27, vol. 3, No. 1, Cold Spring Harbor Laboratory Press, Woodbury, NY, US.

Mullis et al., "Specific synthesis of DNA in vitro via a polymerase-catalyzed chain reaction", Methods in Enzymology, 1987, pp. 335-350, vol. 155, Academic Press, Inc., Elsevier Inc., Philadelphia, PA, US.

Reed et al., "High-resolution DNA melting analysis for simple and efficient molecular diagnostics," Pharmacogenomics, Jun. 2007, pp. 597-608, vol. 8, No. 6, Future Medicine Ltd, London, United Kingdom.

Stratagene, Mx3000P™ Real-Time PCR System, Instruction Manual (2004).

Walker et al. "Isothermal in vitro amplification of DNA by a restriction enzyme/DNA polymerase system," Proc. Natl. Acad. Sci., Jan. 1, 1992, pp. 392-396, vol. 89, No. 1, Proc. Natl. Acad. Sci, USA.

Walker et al. "Strand displacement amplification—an isothermal, in vitro DNA amplification technique," Nucleic Acids Res., 1992, pp. 1691-1696, vol. 20, No. 7, Oxford University Press, Oxford, UK.

Zhang, Modern Molecular Biology Laboratory Manual, 2000, pp. 255-260, Science Publishers, USA.

APO Notice of Acceptance, Australian Patent Application No. 2013202808, dated Nov. 4, 2014.

APO Patent Examination Report No. 1, Australian Patent Application No. 2013202808, dated Mar. 3, 2014.

CIPO Office Action, Canadian Patent Application No. 2,879,720, dated Mar. 6, 2015.

CIPO, Exam Report, Canadian Patent Application No. 2,879,720, dated Jul. 23, 2015.

CIPO, Notice of Allowance, Canadian Patent Application No. 2,879,720, dated Aug. 28, 2015.

EPO Extended European Search Report, European Patent Application No. 16193348.6, dated Nov. 7, 2016.

EPO Communication pursuant to Article 94(3) EPC, European Patent Application No. 16193348.6, dated Feb. 26, 2019.

(56) References Cited

OTHER PUBLICATIONS

PCT Search Report, International Application No. PCT/US2013/053021, dated Dec. 13, 2013.
PCT Written Opinion, International Application No. PCT/US2013/053021, dated Dec. 13, 2013.
PCT International Preliminary Examination Report, International Application No. PCT/US2013/053021, dated Feb. 3, 2015.
USPTO Non-Final Office Action, U.S. Appl. No. 13/956,060, dated Mar. 19, 2015.
USPTO Final Office Action, U.S. Appl. No. 13/956,060, dated Oct. 15, 2015.
USPTO Non-Final Office Action, U.S. Appl. No. 13/956,060, dated Apr. 27, 2016.
USPTO Notice of Allowance, U.S. Appl. No. 13/956,060, dated Oct. 26, 2016.
EPO Communication Pursuant to Article 94(3) EPC, European Patent Application 16193348.6, dated Sep. 30, 2019.

* cited by examiner

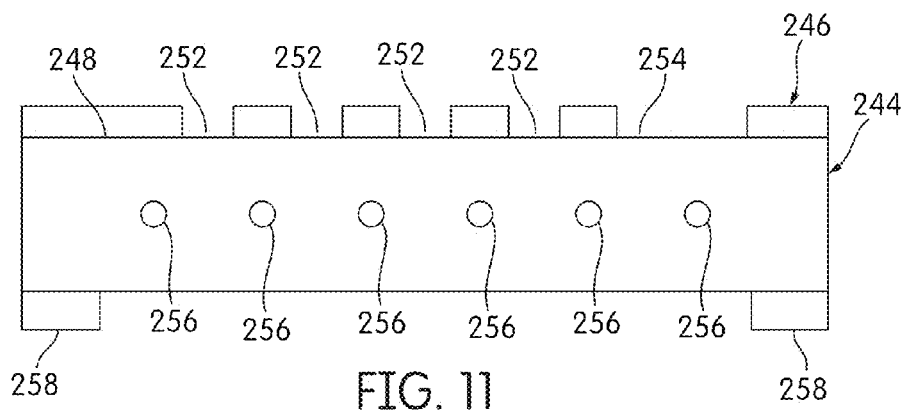
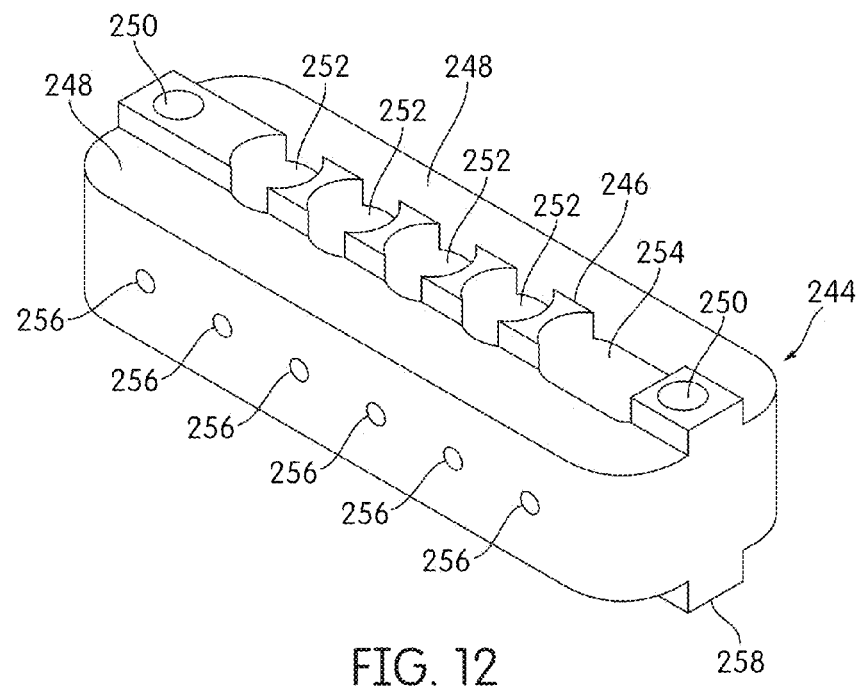

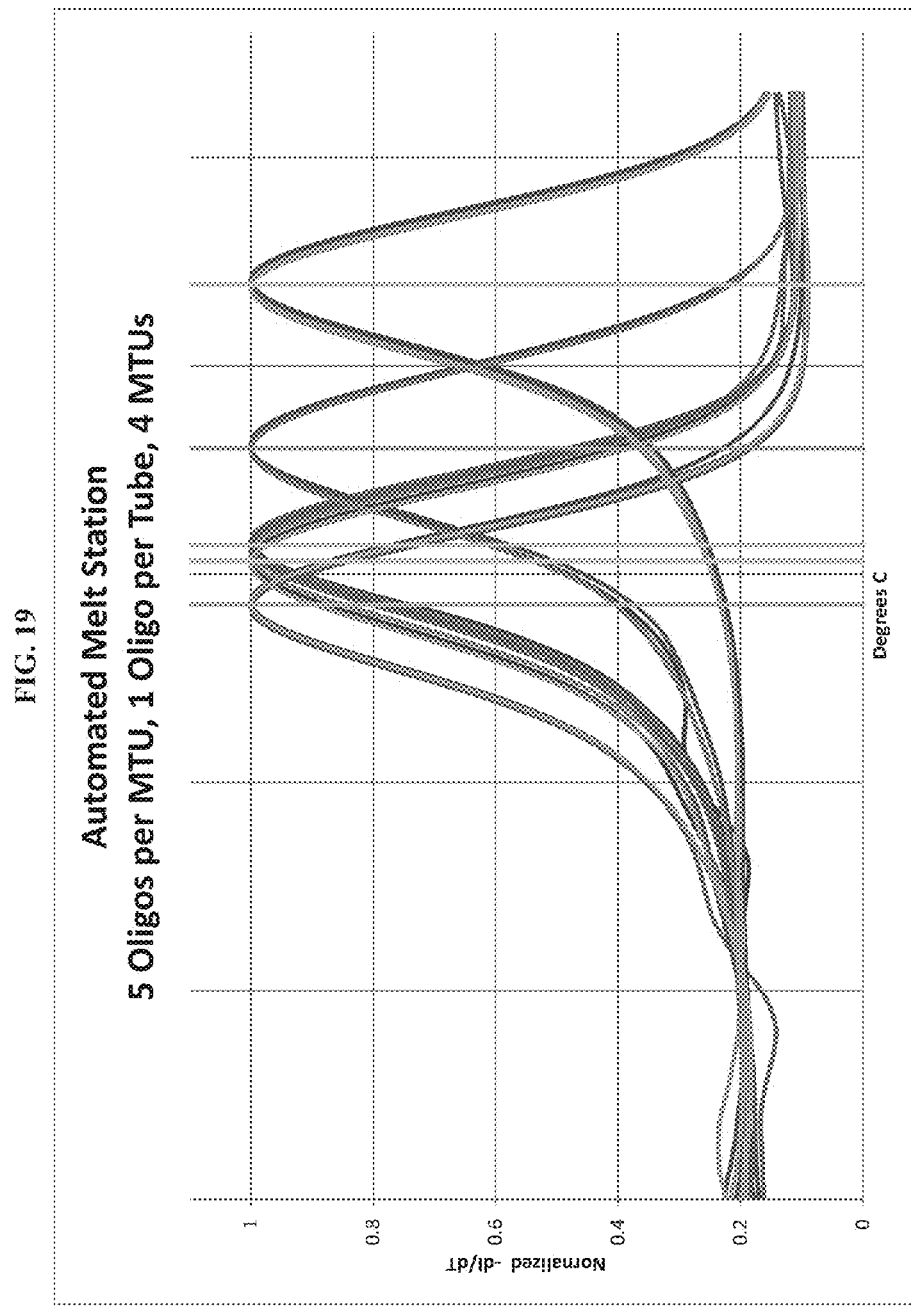

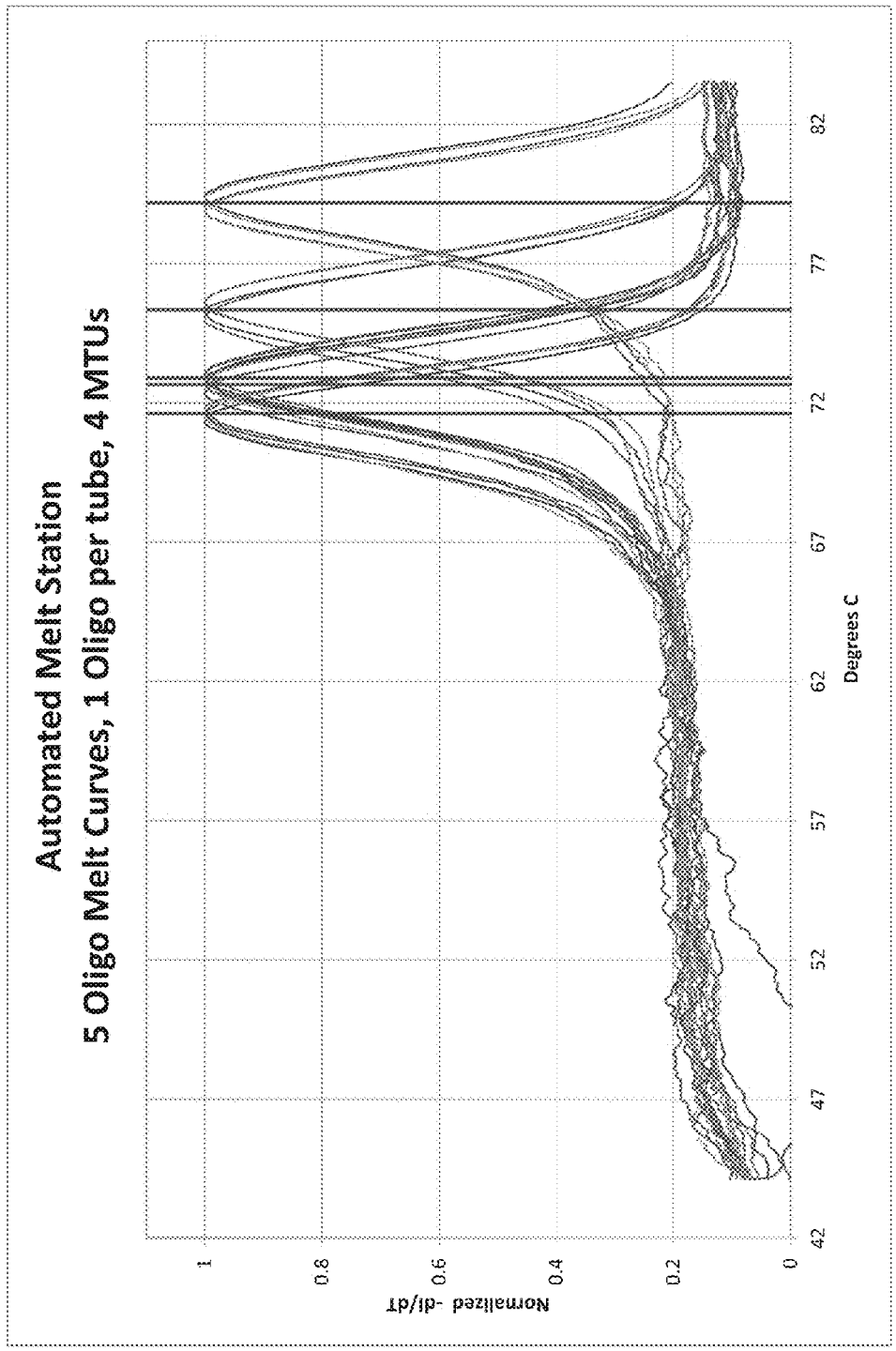

APPARATUS AND SYSTEM FOR PERFORMING THERMAL MELT ANALYSES AND AMPLIFICATIONS

CROSS-REFERENCE TO RELATED APPLICATIONS

This application is a divisional of U.S. application Ser. No. 13/956,060, filed Jul. 31, 2013, now U.S. Pat. No. 9,588,069, which claims the benefit of U.S. Provisional Application No. 61/677,790, filed Jul. 31, 2012, the contents of each of which applications is hereby incorporated by reference herein in its entirety.

FIELD

The present invention relates to systems and methods for performing multiple thermal melt analysis procedures in each of a plurality of reaction receptacles.

BACKGROUND

None of the references described or referred to herein are admitted to be prior art to the claimed invention.

Diagnostic assays are widely used in clinical diagnosis and health science research to detect or quantify the presence or amount of biological antigens, cell or genetic abnormalities, disease states, and disease-associated pathogens or genetic mutations in an organism or biological sample. Where a diagnostic assay permits quantification, practitioners may be better able to calculate the extent of infection or disease and to determine the state of a disease over time. Diagnostic assays are frequently focused on the detection of chemicals, proteins or polysaccharides antigens, nucleic acids, biopolymers, cells, or tissue of interest. A variety of assays may be employed to detect these diagnostic indicators.

Nucleic acid-based assays, in particular, generally include multiple steps leading to the detection or quantification of one or more target nucleic acid sequences in a sample. The targeted nucleic acid sequences are often specific to an identifiable group of cells, tissues, organisms, or viruses, where the group is defined by at least one shared sequence of nucleic acid that is common to members of the group and is specific to that group in the sample being assayed. A variety of nucleic acid-based detection methods are fully described by Kohne, U.S. Pat. No. 4,851,330, and Hogan, U.S. Pat. No. 5,541,308, the disclosures of each of which are hereby incorporated by reference.

A nucleic acid-based assay is performed, for example, in part by exposing a sample to a probe configured to exhibit specificity, under particular hybridization conditions, for a nucleic acid sequence belonging to the protein, cell, tissue, organism, or virus of interest. The sample is frequently treated in some manner to extract nucleic acids in a manner that they are eligible for hybridization.

Before or after exposing the target nucleic acid to a probe, the target nucleic acid can be immobilized by target-capture means, either directly or indirectly, using a "capture probe" bound to a substrate, such as a magnetic bead. Target capture probes are generally short nucleic acid sequences (i.e., oligonucleotide) capable of hybridizing with a sequence of nucleic acid that contains the target sequence. When magnetic beads comprise capture probes, magnets in close proximity to the reaction vessel are used to draw and hold the magnetic beads to the side of the vessel. Once the target nucleic acid is thus immobilized, the hybridized nucleic acid can be separated from non-hybridized nucleic acid present in the sample by, for example, aspirating fluid from the reaction vessel and optionally performing one or more wash steps.

In most instances, it is desirable to amplify the target sequence using any of several nucleic acid amplification procedures which are well known in the art. Methods of nucleic acid amplification are thoroughly described in the literature. PCR amplification, for instance, is described by Mullis et al. in U.S. Pat. Nos. 4,683,195, 4,683,202 and 4,800,159, and in *Methods in Enzymology*, 155:335-350 (1987), the disclosure of each of which is hereby incorporated by reference. Examples of SDA can be found in Walker, *PCR Methods and Applications*, 3:25-30 (1993), Walker et al. in *Nucleic Acids Res.*, 20:1691-1996 (1992) and *Proc. Natl. Acad. Sci.*, 89:392-396 (1991). LCR is described in U.S. Pat. Nos. 5,427,930 and 5,686,272, the disclosure of each of which is hereby incorporated by reference. Examples of transcription-associated amplification ("TAA") formats are provided, for example, in Burg et al. in U.S. Pat. No. 5,437,990; Kacian et al. in U.S. Pat. Nos. 5,399,491 and 5,554,516; and Gingeras et al. in International Application No. PCT/US87/01966 (published as International Publication No. WO 88/01302), and International Application No. PCT/US88/02108 (published as International Publication No. WO 88/10315), the disclosure of each of which is hereby incorporated by reference.

Detection of a targeted nucleic acid sequence frequently requires the use of a nucleic acid molecule having a nucleotide base sequence that is substantially complementary to at least a portion of the targeted sequence or its amplicon. Under selective assay conditions, the probe will hybridize to the targeted sequence or its amplicon in a manner permitting a practitioner to detect the presence of the targeted sequence in a sample. Techniques of effective probe preparation are known in the art. In general, however, effective probes are designed to prevent non-specific hybridization with itself or any nucleic acid molecule that will interfere with detecting the presence of the targeted sequence. Probes may include, for example, a label capable of detection, where the label is, for example, a radiolabel, a fluorophore or fluorescent dye, biotin, an enzyme, a chemiluminescent compound, or another type of detectable signal known in the art.

Because the probe hybridizes to the targeted sequence or its amplicon in a manner permitting detection of a signal indicating the presence of the targeted sequence in a sample, the strength of the signal is proportional to the amount of target sequence or its amplicon that is present. Accordingly, by periodically measuring, during the amplification process, a signal indicative of the presence of amplicon, the growth of amplicon overtime can be detected. Based on the data collected during this "real-time" monitoring of the amplification process, the amount of the target nucleic acid that was originally in the sample can be ascertained. Systems and methods for real time detection and for processing real time data to ascertain nucleic acid levels are described, for example, in Lair, et al., U.S. Pat. No. 7,932,081, "Signal Measuring System for Conducting Real-Time Amplification Assays," the disclosure of which is hereby incorporated by reference.

To detect different nucleic acids of interest in a single assay, different probes configured to hybridize to different nucleic acids, each of which may provide detectibly different signals can be used. For example, different probes configured to hybridize to different targets can be formulated with fluorophores that fluoresce at a predetermined wavelength when exposed to excitation light of a prescribed excitation wavelength. Assays for detecting different target nucleic acids can be performed in parallel by alternately exposing the sample material to different excitation wavelengths and detecting the level of fluorescence at the wavelength of interest corresponding to the probe for each target nucleic acid during the real-time monitoring process. Parallel processing can be performed using different signal detecting devices constructed and arranged to periodically measure signal emissions during the amplification process, and with different signal detecting devices being configured to generate excitation signals of different wavelengths and to measure emission signals of different wavelengths. Suitable signal detecting devices include fluorometers, such as the fluorometer described below.

Thermal melt analysis, or melting curve analysis, encompasses an assessment of the dissociation-characteristics of double-stranded DNA during heating to identify specific genotypes within a target nucleic acid. The information gathered can be used to infer the presence and identity of single-nucleotide polymorphisms. More specifically, the energy required to break the base-base hydrogen bonding between two strands of DNA is dependent on their length, GC-content (or guanine-cytosine content), and their complementarity. By heating a reaction-mixture that contains double-stranded DNA sequences and measuring dissociation against temperature, a variety of attributes can be inferred. Originally strand dissociation was observed using UV absorbance measurements, but techniques based on fluorescence measurements are now the most common approach. The temperature-dependent dissociation between two DNA-strands can be measured using a DNA-intercalating fluorophore, such as SYBR green, EvaGreen or fluorophore-labeled DNA probes. In the case of SYBR green, the dissociation of the DNA during heating is measurable by the large reduction in fluorescence that results. Alternatively, juxtapositioned probes, one featuring a fluorophore and the other featuring a suitable quencher can be used to determine the complementarity of the probe to the target sequence. For example, though a variety of other methods are known in the art, a graph of the negative first derivative of the melting-curve may make it easier to pin-point the temperature of dissociation (defined as 50% dissociation), by virtue of the peaks thus defined.

Melt curve analysis describes a method where the temperature dependent dissociation of two strands of nucleic acids is measured. To perform the melt curve analysis, the temperature of a sample, and/or an amplicon contained therein, is raised while monitoring a signal emitted by the sample, such as the fluorescence of a fluorophore labeled probe. As the temperature rises, the dissociation of the probe and the amplicon can be measured as detectable change in the signal, such as by a decrease in fluorescence. A melt station holds one or more receptacles containing sample materials, e.g., amplicon, and subjects the contents of the receptacles to thermal energy to raise the temperature of the amplicon along a controlled temperature profile while monitoring signal, e.g., fluorescence, emitted by the contents. Where the detected signal is fluorescence, the fluorescence may be monitored in one or more wavelengths. The procedure results in a melt curve of fluorescence vs. time. Differences in the melt temperature can be used to discriminate variations in the sequence of the amplicon. For example, the mutant and wild type strands may exhibit markedly different melt temperatures.

Typically, thermal melt analysis is performed on molecular diagnostic instruments that process samples in batch. A group of samples, i.e., the "batch," is placed in the instrument—typically a thermal block, and the instrument is operated to perform the thermal melt and the thermal melt analysis on all samples substantially simultaneously. Instrument operation continues until the assay has been completed for all samples placed in the instrument. After completion of the assay, the operation of the instrument is stopped, or paused, the batch of samples is removed, the temperature of the instrument, or thermal block, is ramped down to a particular starting temperature, and then a subsequent batch of samples may be placed in the instrument and the process repeated.

Typically melt analysis is performed by placing a receptacle holding a reaction liquid into an instrument which ramps the temperature of the reaction liquid up by ramping the temperature of a component, often referred to as a thermal, block, of the instrument. The temperature of the block is ramped, according to a pre-defined temperature profile, slowly enough so that the temperature of the reaction liquid accurately follows the temperature of the block. The temperature of the block can be changed slowly and linearly, or it can be changed in stepwise fashion while holding the temperature of each step long enough for the reaction liquid to reach steady state at each temperature step. The temperature of the block must start at or below the lowest analysis temperature and end at or above the highest analysis temperature to ensure that the temperature of the reaction liquid is known throughout the melting process. To get ready for the next receptacle, i.e., batch, the temperature of the block must ramp down to the start temperature. The total throughput of the instrument is limited by the speed at which the temperature of the reaction liquid can be changed from the start temperature to the end temperature and the speed at which the temperature of the block can be returned back to the start temperature to get ready for the next batch. The analysis time is also limited by the speed at which the temperature of the reaction liquid within the receptacle can follow the block temperature.

Other diagnostic instruments process samples in a serial (also known as a linear or pipeline) manner, as opposed to a batch manner. Samples are sequentially and continuously processed through the instrument, with different steps of the process being performed on different samples in a parallel manner. One sample may be completing the assay process, while another is just beginning the process. Thus, processing on all the samples is not started or completed at the same time, and assays may be completed on a periodic basis, for example, once every five minutes, during operation of the instrument.

For automated instruments that process samples in a serial fashion, in order to maintain an exemplary sequence of completing one sample assay every five minutes, or other desired interval, the melt station must be able to process one reaction receptacle at a time and complete the thermal melt cycle in preferably one five-minute interval. If the thermal melt station is not able to maintain the desired frequency by completing the thermal melt cycle within the specified time interval, it becomes necessary to employ two, or more, thermal melt stations operating in parallel. The need to slowly ramp the temperature from the starting temperature to the ending temperature and then back to the starting temperature, as described above, as well as the time lag that may be required for the contents of the receptacle to reach thermal equilibrium with the thermal block creates a challenge to design a thermal melt station that can complete the thermal melt procedure within the time interval needed to maintain the desired through put of a serial-processing molecular diagnostic instrument.

SUMMARY

Aspects of the invention are embodied in an apparatus configured to apply thermal energy to the contents of a receptacle to increase the temperature of the contents of the receptacle and to detect an optical signal emitted by the contents of the receptacle as the temperature of the contents is rising. The apparatus comprises a receptacle holder configured to receive and releasably hold a receptacle, a vessel-receiving thermal assembly including a portion thereof held at a constant elevated temperature relative to ambient temperature and configured to receive a portion of the receptacle and to apply thermal energy to the contents of the receptacle, a receptacle moving mechanism configured to effect relative movement between the receptacle holder and the vessel-receiving thermal assembly to place a portion of the receptacle held by the receptacle holder into the vessel-receiving thermal assembly and to remove the portion of the receptacle from the vessel-receiving thermal assembly; and an optical signal detecting device constructed and arranged to detect optical signals emitted by the contents of a receptacle held within the vessel-receiving thermal assembly while thermal energy is being applied to the contents by the vessel-receiving thermal assembly.

According to further aspects the receptacle holder comprises a cover positioned over a receptacle carried in the receptacle holder and a yoke comprising side walls along opposed sides of the yoke and lateral support flanges extending along bottom edges of the sides walls.

According to further aspects, the apparatus further comprising a receptacle present detector configured to detect the presence of a receptacle in the receptacle holder.

According to further aspects, the receptacle moving mechanism is controlled by a system controller configured to initiate the relative movement between the receptacle holder and the vessel-receiving thermal assembly when the receptacle present detector detects the presence of a receptacle in the receptacle holder.

According to further aspects, the vessel-receiving thermal assembly comprises a vessel alignment block and a thermal block. The vessel alignment block is constructed and arranged to position a portion of a receptacle carried by the receptacle holder into the thermal block when the receptacle moving mechanism effects relative movement between the receptacle holder and the vessel-receiving thermal assembly.

According to further aspects, the thermal block is configured to be held at the constant elevated temperature.

According to further aspects, the apparatus further comprising a thermal element in thermal contact with the thermal block.

According to further aspects, the thermal element comprise a resistive foil covering at least a portion of the thermal block.

According to further aspects, the vessel alignment block comprises an alignment opening formed therein and configured to hold a receptacle inserted through the opening in a fixed orientation. Further, the thermal block formed is formed from a thermally conductive material and comprises a receptacle opening formed therein. The thermal block is positioned with respect to the vessel alignment block so that the receptacle opening formed in the thermal block is aligned with the alignment opening formed through the vessel alignment block so that a receptacle inserted through the alignment opening formed through the vessel alignment block is positioned within the receptacle opening formed in the thermal block.

According to further aspects, the apparatus comprises at least one signal hole formed in the thermal block and extending into the receptacle opening formed therein. The signal hole is configured to enable the optical signal detecting device to detect optical signals emitted by the contents of a receptacle positioned within the receptacle opening.

According to further aspects, that apparatus comprises an interface block disposed between the vessel alignment block and the thermal block and having an opening aligned with the alignment opening of the vessel alignment block and the receptacle opening of the thermal block.

According to further aspects, the alignment opening formed through the vessel alignment block is circular in cross-section and the receptacle opening formed in the thermal block is circular in cross section.

According to further aspects, the vessel alignment block comprises a raised center portion extending longitudinally of the vessel alignment block across a top surface of the vessel alignment block and defining recess shoulder portions on opposite sides of the raised center portion.

According to further aspects, the thermal block comprises one or more receptacle holes formed therein from a top surface of the thermal block and a hollowed-out portion extending from a lower surface of the block and surrounding the one or more receptacle holes without extending into any of the receptacle holes.

According to further aspects, the apparatus comprises a bottom cover secured to a bottom surface of the thermal block to substantially enclose the hollowed-out portion.

According to further aspects, the apparatus comprises signal holes formed in the thermal block and the bottom cover and extending into the receptacle holes formed in the thermal block. The signal holes are configured to enable the optical signal detecting device to detect optical signals emitted by the contents of receptacles positioned within the receptacle holes.

According to further aspects, the vessel alignment block includes one or more mounting blocks raised from a surface thereof at which the vessel alignment block is attached to the thermal block.

According to further aspects, the receptacle holder is configured to receive and releasably hold a plurality of receptacles. The vessel-receiving thermal assembly is configured to receive a portion of a plurality of receptacles and to apply thermal energy to the contents of the receptacles. The apparatus further includes a detector translating mechanism constructed and arranged to move the optical signal detecting device with respect to the vessel-receiving assembly to selectively position a signal detecting channel of the signal detecting device in detecting alignment with two or more different receptacles held within the vessel-receiving thermal assembly.

According to further aspects, the receptacle moving mechanism comprises a motor, a threaded drive screw coupled to an output shaft of the motor; and a screw follower coupled to the receptacle holder. The drive screw is engaged with the screw follower such that powered rotation of the drive screw by the motor causes translation of the receptacle holder.

According to further aspects, the apparatus comprises an encoder coupled to the motor and the threaded drive screw for monitoring a position of the receptacle holder and one or more positions sensors, each position sensor being configured to detect a predetermined position of the receptacle holder.

According to further aspects, each position sensor comprises a slotted optical sensor configured to be activated by a tab projecting from a portion of the receptacle holder or the receptacle moving mechanism.

According to further aspects, the screw follower is attached to a translating support bracket to which the receptacle holder is attached.

According to further aspects, the apparatus comprises one or more isolation mounts disposed between the translating support bracket and the receptacle holder. Each isolation mount comprises a pin extending from the translating support bracket though an opening formed in the receptacle holder and a coil spring coaxially surrounding the pin.

According to further aspects, the vessel does not physically contact the thermal block.

According to further aspects, the optical signal detecting device is configured to detect optical signals at two or more distinct and distinguishable wavelengths.

According to further aspects, the optical signal detecting device is configured to detect optical signals at six (6) distinct and distinguishable wavelengths.

According to further aspects, the receptacle holder and the vessel-receiving thermal assembly are configured such that the portion of the receptacle held by the receptacle holder placed into the vessel-receiving thermal assembly is less than half of the receptacle.

According to further aspects, the apparatus comprises a signal detecting device moving mechanism constructed and arranged to move the optical signal detecting device with respect to vessel-receiving thermal assembly.

According to further aspects, the optical signal detecting device comprises two or more channels, each channel being configured to detect an optical signal at a distinct and distinguishable wavelength, and wherein the signal detecting device moving mechanism is constructed and arranged to sequentially position each channel relative to the receptacle to enable the signal detecting device to sequentially detect the wavelength corresponding to each channel.

According to further aspects, the signal detecting device moving mechanism comprises a motor, a threaded drive screw coupled to an output shaft of the motor, and a screw follower coupled to the optical signal detecting device. The drive screw is engaged with the screw follower such that powered rotation of the drive screw by the motor causes translation of the optical signal detecting device.

According to further aspects, the apparatus comprises an encoder coupled to the motor and the threaded drive screw for monitoring a position of the optical signal detecting device and one or more positions sensors, each position sensor being configured to detect a predetermined position of the optical signal detecting device.

According to further aspects, each position sensor comprises a slotted optical sensor configured to be activated by a tab projecting from a portion of the optical signal detecting device or the signal detecting device moving mechanism.

Further aspects of the invention are embodied in a system for performing a nucleic acid diagnostic assay on a sample carried within a receptacle. The system comprises a target isolation module configured to isolate a target nucleic acid within the sample and to separate the target nucleic acid from non-target components of the sample, an incubation module configured to incubate the contents of a receptacle and perform an amplification procedure on the separated target nucleic acid within the receptacle, a thermal melt analysis module configured to receive a receptacle and to increase the temperature of the contents of the receptacle from a first temperature to a second temperature and to detect and record an optical signal emitted by the contents of the receptacle while the temperature of the contents is rising from the first temperature to the second temperature. The thermal melt analysis module includes a thermal block maintained at a substantially constant temperature that is greater than the first temperature. The temperature of the contents of the receptacle is increased from the first temperature to the second temperature by placing a receptacle having contents that are initially at the first temperature into operative proximity to the thermal block so that heat energy from the thermal block increases the temperature of the contents of the receptacle from the first temperature to the second temperature. The system further includes a receptacle transport mechanism under computer control and configured to (1) provide a receptacle containing a sample to the target isolation module, (2) after the target nucleic acid has been separated from non-target components of the sample, remove the receptacle from the target isolation module, (3) after removing the receptacle from the target isolation module, provide the receptacle to the incubation module, (4) after the amplification procedure is complete, remove the receptacle from the incubation module, and (5) after removing the receptacle from the incubation module, provide the receptacle to the thermal melt analysis module.

Further aspects of the invention are embodied in a method for performing a thermal melt analysis within a thermal melt analysis module. The method comprises the steps of (a) maintaining a thermal block within the module at a steady-state temperature, (b) placing a receptacle within the module in thermal contact with the thermal block, wherein the receptacle has contents that are at an initial temperature that is lower than the steady-state temperature, (c) allowing the receptacle to dwell in thermal contact with the thermal block for at least a predetermined dwell period so that the temperature of the contents of the receptacle increases from the initial temperature to a temperature that is higher than the initial temperature, (d) while the temperature of the contents of the receptacle is increasing from the initial temperature to the temperature that is above the initial temperature, measuring an optical signal emitted from the contents of the receptacle, and (e) detecting a change in the measured optical signal as the temperature of the contents of the receptacle increases from the initial temperature to the temperature that is above the initial temperature.

According to further aspects, the method comprises the step of removal of the receptacle from the module, and steps (b)-(e) and receptacle removal are repeated with two or more receptacles, and the temperature of the thermal block does not appreciably change from the steady state-temperature during or between repeating steps (b)-(e) with the two or more receptacles.

According to further aspects, the steady-state temperature is at least about 90° C.

According to further aspects, the steady-state temperature is between about 70° C. and about 120° C.

According to further aspects, the steady-state temperature is between about 70° C. and about 90° C.

According to further aspects, the change in the measured optical signal results from melting of the hydrogen bonds between hybridized nucleic acid sequences contained in the receptacle. Although nucleic acid melting is exemplified herein, the present apparatuses and methods are also useful in conducting melting analyses of a variety of polymers, including amino acid and nucleic acid based polymers such as polypeptides, proteins, and various length nucleic acid molecules.

According to further aspects, the method comprises removal of the receptacle from the module, and wherein steps (b)-(f) and receptacle removal are accomplished in less than about 5 minutes.

According to further aspects, the step of detecting a change in the measured optical signal comprises computing a derivative of the optical signal with respect to temperature and identifying an inflection point in the optical signal.

According to further aspects, multiple different optical signals emitted from the contents of the receptacle are monitored.

Further aspects of the invention are embodied in a method for performing a thermal melt analysis of a sample within a steady-state temperature module without actively monitoring the temperature of the sample. The method comprises the steps of (a) maintaining a thermal block within the module at a steady-state temperature, (b) introducing the receptacle to the module, wherein the receptacle is placed in thermal contact with the thermal block, and wherein the receptacle has contents that are at an initial temperature that is lower than the steady-state temperature, (c) allowing the receptacle to dwell in thermal contact with the thermal block so that the temperature of the contents of the receptacle increases from the initial temperature to a temperature that is higher than the initial temperature, and measuring the elapsed time that the receptacle is in thermal contact with the thermal block, (d) while the temperature of the contents of the receptacle is increasing from the initial temperature to the temperature that is above the initial temperature, detecting an optical signal attributable to a calibrator present in the contents of the receptacle, wherein the calibrator generates a detectable signal when the calibrator is at a predetermined temperature, (e) measuring the elapsed time between introducing the receptacle to the module and the detection of the optical signal attributable to the calibrator, and (f) comparing the measured elapsed time between introducing the receptacle to the module and the detection of the optical signal attributable to the calibrator to a calibration curve to determine the temperature of the contents of the receptacle at any time while the receptacle is present in the module, wherein the calibration curve comprises a plot of time versus temperature.

According to further aspects, the temperature of the contents of the receptacle is not actively monitored.

According to further aspects, the temperature of the receptacle or the contents of the receptacle is not actively monitored.

According to further aspects, the temperature of the receptacle and the contents of the receptacle are not actively monitored.

According to further aspects, the steady-state temperature is at least about 90° C.

According to further aspects, the steady-state temperature is between about 70° C. and about 120° C.

According to further aspects, the steady-state temperature is between about 70° C. and about 90° C.

According to further aspects, the method comprises the step of measuring an optical signal emitted from the contents of the receptacle not attributable to the calibrator.

According to further aspects, the method comprises the step of measuring multiple optical signals emitted from the contents of the receptacle not attributable to the calibrator.

According to further aspects, the method comprises the step of detecting optical signals attributable to two or more different calibrators, wherein each of the two or more different calibrators generates a detectable signal when the calibrator is at a predetermined temperature.

Other features and characteristics of the present invention, as well as the methods of operation, functions of related elements of structure and the combination of parts, and economies of manufacture, will become more apparent upon consideration of the following description and the appended claims with reference to the accompanying drawings, all of which form a part of this specification, wherein like reference numerals designate corresponding parts in the various figures.

DESCRIPTION OF THE DRAWINGS

FIG. 11 is a side view of a vessel alignment block of a vessel-receiving thermal assembly of the thermal melt module.

FIG. 12 is a perspective view of the vessel alignment block.

FIG. 19 is a plot of the derivatives of fluorescence signals with respect to temperature for four different targets across multiple runs, in multiple receptacles, and in different locations, within an exemplary thermal module.

FIG. 20 is a plot of the derivatives of fluorescence signals with respect to temperature for four different reduced-concentration targets across multiple runs, in multiple receptacles, and in different locations, within an exemplary thermal module.

DETAILED DESCRIPTION

Overview

Unless defined otherwise, all terms of art, notations and other scientific terms or terminology used herein have the same meaning as is commonly understood by one of ordinary skill in the art to which this disclosure belongs. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted. All patents, applications, published applications and other publications referred to herein are incorporated by reference in their entirety. If a definition set forth in this section is contrary to or otherwise inconsistent with a definition set forth in the patents, applications, published applications, and other publications that are herein incorporated by reference, the definition set forth in this section prevails over the definition that is incorporated herein by reference.

As used herein, "a" or "an" means "at least one" or "one or more."

Automated Analyzer

Figure 1:
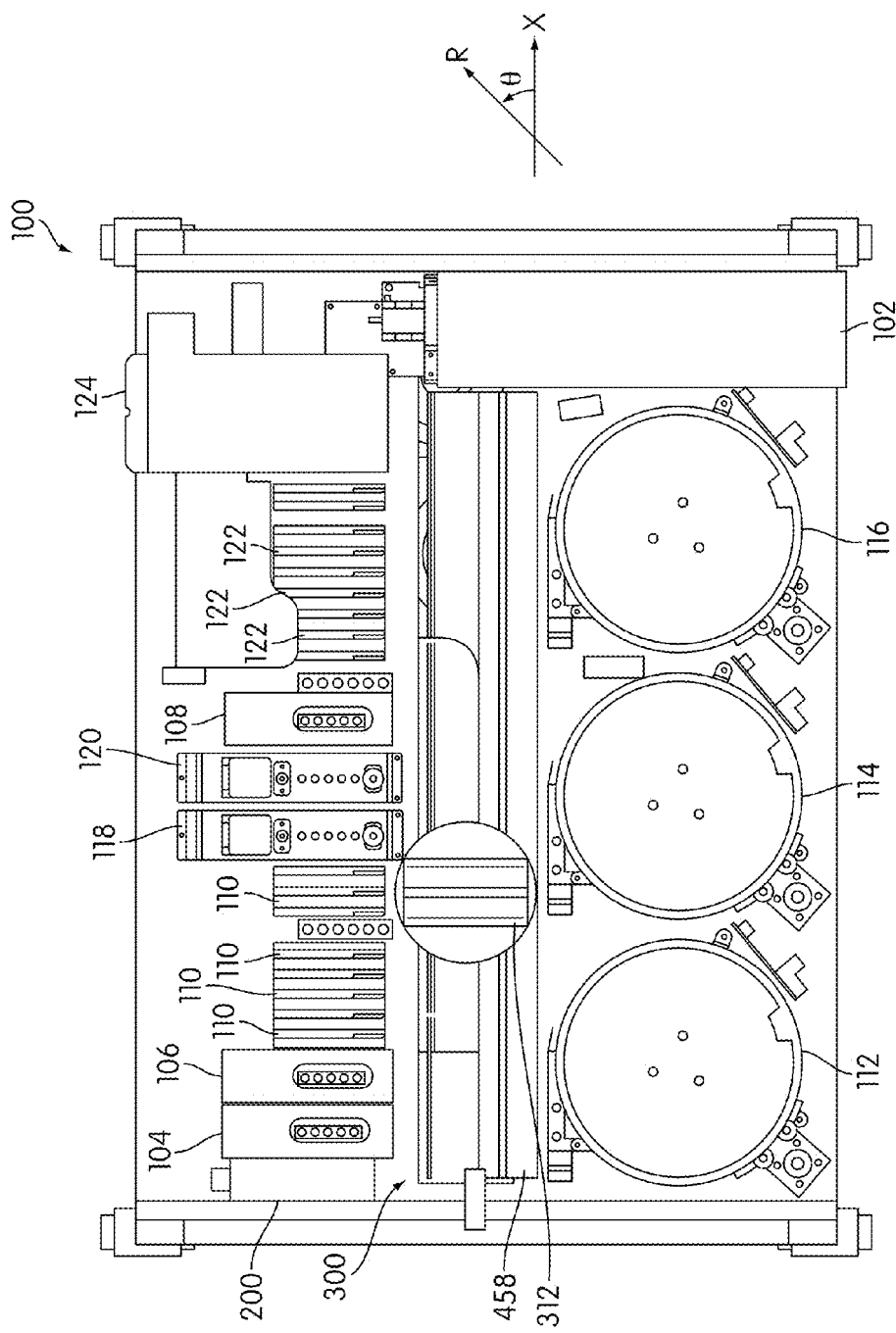
FIG. 1 is a plan view of an analyzer including various modules configured to receive one or more reaction receptacles, within each of which one or more steps of a molecular diagnostic assay or other biological or chemical process may be performed. A receptacle transfer apparatus is incorporated for transferring reaction receptacles between the various modules and inserting reaction receptacles into and removing reaction receptacles from the modules.

An analyzer in which the method and apparatus of the present invention may be implemented is shown schematically in plan view and designated by reference number 100 in FIG. 1. The analyzer 100 includes various modules configured to receive one or more reaction receptacles (described in more detail below) within each of which is performed one or more steps of a multi-step analytical process, such as a nucleic acid test (NAT), or other chemical, biochemical or biological process. The modules of the analyzer 100 constitute receptacle-receiving structures configured to receive and hold one or more reaction receptacles.

In one embodiment, an exemplary analyzer in which the present invention may be implemented may include a receptacle input module 102 including structure for receiving and holding one or more empty reaction receptacles prior to the receptacles being used for performing a chemical, biological, or other multi-step process. The receptacle input module 102 may comprise a drawer or cabinet holding a plurality of receptacles and may include a receptacle feeding apparatus for moving receptacles, e.g., one or more at a time, into a receptacle pick-up position. In certain preferred embodiments, the receptacle pick-up position comprises a registered or known position of the receptacle to facilitate removal of the receptacle by receptacle distributor 300.

Analyzer 100 may further include various containers for holding bulk fluids, such as water, buffer solution, and waste materials. Other modules may be provided for holding containers of reaction fluids, such as reagents, and such modules may be constructed and arranged to maintain the contents of such containers at prescribed storage temperatures and/or to agitate such containers to maintain the contents of the containers in solution or suspension. Analyzer 100 may further include a sample loading module constructed and arranged to receive and hold containers, such as test tubes, containing sample specimens. Fluid transfer apparatuses may be provided for transferring fluids, e.g., sample fluids, reagents, bulk fluids, waste fluids, etc., to and from reaction receptacles. Such fluid transfer apparatuses may comprises one or more robotic pipettor apparatuses configured for controlled, automated movement and access to the reaction receptacles and containers holding reaction fluids and/or bulk fluids and containers holding sample specimens. Fluid transfer apparatuses may also include fluid dispensers, e.g., nozzles, disposed within other modules and connected by suitable fluid conduits to containers, e.g., bulk fluid containers, and to pumps or other apparatus for causing fluid movement from the containers to the dispensers.

Analyzer 100 may further include load stations 104, 106, 108 configured to receive a reaction receptacle and within which one or more materials may be added to the receptacles, including sample material and various reaction reagents by a fluid transfer apparatus. In an implementation where the analyzer 100 comprises a platform for performing a NAT, reaction reagents may comprise target capture reagents, nucleic acid amplification reagents, and/or nucleic acid detection reagents.

Analyzer 100 may further comprise temperature ramping stations 110 configured to hold one or more reaction receptacles in an environment that is maintained at higher than ambient temperatures so as to raise the temperature of the contents of the receptacles. Exemplary temperature ramping stations are described in U.S. Patent Application Publication No. 2008-0089818, entitled "System and Method for Incubating the Contents of a Reaction Receptacle," the disclosure of which is hereby incorporated by reference. Analyzer 100 may further include one or more incubators. The illustrated analyzer 100 includes three incubators 112, 114, 116, each of which is configured to receive a plurality of reaction receptacles and maintain the receptacles in an elevated temperature environment. Exemplary incubators are described in U.S. Pat. No. 7,964,413, entitled "Method for Continuous Mode Processing of the Contents of Multiple Reaction Receptacles in a Real-Time Amplification Assay" and U.S. patent application Ser. No. 13/404,437 (U.S. Patent Application Publication No. US20120221252), entitled "Systems and Methods for Distinguishing Optical Signals of Different Modulation Frequencies in an Optical Signal Detector," the respective disclosures of which are hereby incorporated by reference.

Also, in an implementation in which the analyzer 100 comprises a platform for performing a NAT, the analyzer may include sample-processing modules, such as magnetic separation wash stations 118, 120 adapted to separate or isolate an analyte of interest (e.g., a target nucleic acid) bound to a magnetically-responsive target capture material from the remaining contents of the receptacle. Exemplary magnetic separation wash stations are described in U.S. Patent Application Publication No. 2010/0288395, entitled "Method and Apparatus for Effecting Automated Movement of a Magnet in an Instrument for Performing a Magnetic Separation Procedure" and U.S. Pat. No. 6,605,213, entitled "Method and Apparatus for Performing a Magnetic Separation Purification Procedure on a Sample Solution," the respective disclosures of which are hereby incorporated by reference. Analyzer 100 may further include chilling modules 122 adapted to receive one or more reaction receptacles and hold the receptacles in a lower than ambient temperature environment so as to reduce the temperature of the contents of the receptacles. Finally, analyzer 100 may include a detector module 124 adapted to receive a reaction receptacle and detect a signal (e.g., an optical signal) emitted by the contents of the reaction receptacle. In one implementation, detector module 124 may comprise a luminometer for detecting luminescent signals emitted by the contents of a receptacle or a fluorometer for detecting fluorescent emissions. An exemplary luminometer and an exemplary fluorometer are described in previously-incorporated U.S. Pat. No. 7,964,413 and another exemplary fluorometer is described in previously-incorporated U.S. Patent Application Publication No. US20120221252.

Analyzer 100 may further include a thermal melt module 200 embodying aspects of the present invention and which is described in further detail below.

The analyzer 100 further includes a receptacle transfer apparatus, which, in the illustrated embodiment, comprises a receptacle distributor 300, embodying aspects of the present invention. Each of the modules of the analyzer 100 includes a receptacle transfer portal through which receptacles are inserted into or removed from the respective modules. Each module may or may not include an openable door covering its receptacle portal. The receptacle distributor 300 is configured to move receptacles between the various modules and retrieve receptacles from the modules and deposit receptacles into the modules. In one embodiment, the receptacle distributor 300 includes a receptacle distribution head 312 configured to move in an X direction along a transport track assembly 458, rotate in a theta (Θ) direction, and move receptacles in an R direction into and out of the receptacle distribution head 312 and one of the modules of analyzer 100. An exemplary receptacle distributor is described in WO 2010/132885, entitled "Method and Apparatus for Effecting Transfer of Reaction Receptacles in an Instrument for Multi-Step Analytical Procedure," the disclosure of which is hereby incorporated by reference.

Multiple Receptacle Devices

Figure 2:
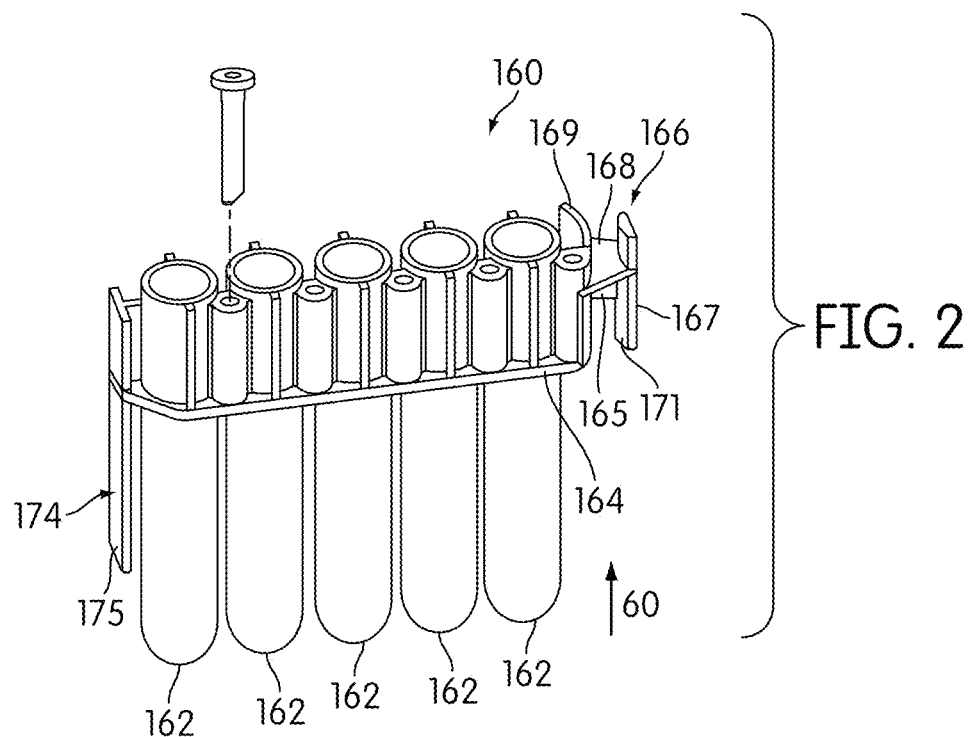
FIG. 2 is a perspective view of a reaction receptacle in the form of a multiple receptacle device unit employed in combination with an apparatus embodying aspects of the present invention.

Referring to FIG. 2, a reaction receptacle in the form of a multiple receptacle device ("MRD") 160 comprises a plurality of individual receptacle vessels, or reaction tubes, 162, preferably five. The receptacle vessels 162, preferably in the form of cylindrical tubes with open top ends and closed bottom ends, are connected to one another by a connecting rib structure 164 which defines a downwardly facing shoulder extending longitudinally along either side of the MRD 160.

Alternatively, the receptacle may comprise any container suitable for holding a fluid or liquid, including a cuvette, beaker, microtiter plate, or test tube. Unless explicitly stated, or the context dictates otherwise, the term "receptacle" will interchangeably refer to an entire MRD, one or more individual receptacle vessels of an MRD, a cuvette, beaker, microtiter plate, test tube, or any other suitable container. Similarly, unless explicitly stated or the context dictates otherwise, descriptions of the invention in the context of an MRD or receptacle vessel of an MRD are exemplary and should not be construed as limiting of the scope of the invention, as aspects of the invention are applicable to any suitable "receptacle."

The MRD 160 is preferably formed from injection molded polypropylene, such as those sold by Montell Polyolefins, of Wilmington, Del., product number PD701NW or Huntsman, product number P5M6K-048. In an alternative embodiment, the receptacle vessels 162 of the MRD are releasably fixed with respect to each other by means such as, for example, a sample tube rack.

An arcuate shield structure 169 is provided at one end of the MRD 160. An MRD manipulating structure 166 extends from the shield structure 169. The manipulating structure is adapted to be engaged by a transport mechanism for moving the MRD 160 between different components of a diagnostic analyzer. An exemplary transport mechanism that is compatible with the MRD 160 is described in U.S. Pat. No. 6,335,166, entitled, "Automated Process for Isolating and Amplifying a Target Nucleic Acid Sequence," the disclosure of which is hereby incorporated by reference. The MRD manipulating structure 166 comprises a laterally extending plate 168 extending from shield structure 169 with a vertically extending piece 167 on the opposite end of the plate 168. A gusset wall 165 extends downwardly from lateral plate 168 between shield structure 169 and vertical piece 167.

Figure 3:
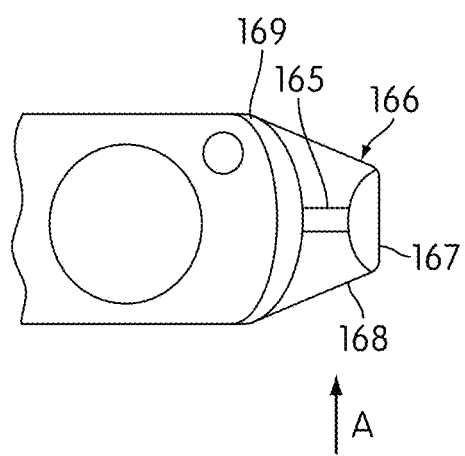
FIG. 3 is an enlarged bottom view of a portion of the multiple receptacle device, viewed in the direction of arrow "60" in FIG. 1.

As shown in FIG. 3, the shield structure 169 and vertical piece 167 have mutually facing convex surfaces. The MRD 160 may be engaged by a transport mechanism and other components, by moving an engaging member laterally (in the direction "A") into the space between the shield structure 169 and the vertical piece 167. The convex surfaces of the shield structure 169 and vertical piece 167 provide for wider points of entry for an engaging member undergoing a lateral relative motion into the space.

A label-receiving structure 174 having a flat label-receiving surface 175 is provided on an end of the MRD 160 opposite the shield structure 169 and MRD manipulating structure 166. Human and/or machine-readable labels, such as scannable bar codes, can be placed on the surface 175 to provide identifying and instructional information on the MRD 160.

Further details regarding the MRD 160 may be found in U.S. Pat. No. 6,086,827, entitled "Reaction Receptacle Apparatus," the disclosure of which is hereby Incorporated by reference.

Nucleic Acid Diagnostic Assays, Apparatus, Systems, and Methods

Aspects of the present invention involve apparatus and procedures that can be used in conjunction with nucleic acid diagnostic assays, including "real-time" amplification assays and "end-point" amplification assays.

Real-time amplification assays can be used to determine the presence and amount of a target nucleic acid in a sample which, by way of example, is derived from a pathogenic organism or virus. By determining the quantity of a target nucleic acid in a sample, a practitioner can approximate the amount or load of the organism or virus in the sample. In one application, a real-time amplification assay may be used to screen blood or blood products intended for transfusion for bloodborne pathogens, such as hepatitis C virus (HCV) and human immunodeficiency virus (HIV). In another application, a real-time assay may be used to monitor the efficacy of a therapeutic regimen in a patient infected with a pathogenic organism or virus, or that is afflicted with a disease characterized by aberrant or mutant gene expression. Real-time amplification assays may also be used for diagnostic purposes, as well as in gene expression determinations. Systems and methods for performing real-time amplification assays are described in U.S. Pat. No. 7,897,337, entitled "Methods for Performing Multi-Formatted Assays," the disclosure of which is hereby incorporated by reference. Systems and methods for end-point detection are described in U.S. Pat. No. 6,335,166, entitled "Automated Process For Isolating and Amplifying a Target Nucleic Acid Sequence," the disclosure of which is hereby incorporated by reference.

In addition to implementation of the invention in conjunction with real-time amplification assays, the invention may also be implemented in conjunction with end point amplification assays. In end-point amplification assays, the presence of amplification products containing the target sequence or its complement is determined at the conclusion of an amplification procedure. The determination may occur in a detection station that may be located externally to the incubator in which the amplification reactions occur. In contrast, in "real-time" amplification assays, the amount of amplification products containing the target sequence or its complement is determined during an amplification procedure. In the real-time amplification assay, the concentration of a target nucleic acid can be determined using data acquired by making periodic measurements of signals that are functions of the amount of amplification product in the sample containing the target sequence, or its complement, and calculating the rate at which the target sequence is being amplified from the acquired data.

In an exemplary real-time amplification assay, the interacting labels include a fluorescent moiety, or other emission moiety, and a quencher moiety, such as, for example, 4-(4-dimethylaminophenylazo) benzoic acid (DABCYL). The fluorescent moiety emits light energy (i.e., fluoresces) at a specific emission wavelength when excited by light energy at an appropriate excitation wavelength. When the fluorescent moiety and the quencher moiety are held in close proximity, light energy emitted by the fluorescent moiety is absorbed by the quencher moiety. But when a probe hybridizes to a nucleic acid present in the sample, the fluorescent and quencher moieties are separated from each other and light energy emitted by the fluorescent moiety can be detected. Fluorescent moieties having different and distinguishable excitation and emission wavelengths are often combined with different probes. The different probes can be added to a sample, and the presence and amount of target nucleic acids associated with each probe can be determined by alternately exposing the sample to light energy at different excitation wavelengths and measuring the light emission from the sample at the different wavelengths corresponding to the different fluorescent moieties. In another embodiment, different fluorescent moieties having the same excitation wavelength, but different and distinguishable emission wavelengths are combined with different probes. The presence and amount of target nucleic acids associated with each probe can be determined by exposing the sample to a specific wavelength light energy and the light emission from the sample at the different wavelengths corresponding to the different fluorescent moieties is measured.

Where an amplification procedure is used to increase the amount of target sequence, or its complement, present in a sample before detection can occur, it is desirable to include a "control" to ensure that amplification has taken place. Such a control can be a known nucleic acid sequence that is unrelated to the sequence(s) of interest. A probe (i.e., a control probe) having specificity for the control sequence and having a unique fluorescent dye (i.e., the control dye) and quencher combination is added to the sample, along with one or more amplification reagents needed to amplify the control sequence, as well as the target sequence(s). After exposing the sample to appropriate amplification conditions, the sample is alternately exposed to light energy at different excitation wavelengths (including the excitation wavelength for the control dye) and emission light is detected. Detection of emission light of a wavelength corresponding to the control dye confirms that the amplification was successful (i.e., the control sequence was indeed amplified), and thus, any failure to detect emission light corresponding to the probe(s) of the target sequence(s) is not likely due to a failed amplification. Conversely, failure to detect emission light from the control dye may be indicative of a failed amplification, thus calling into question the results from that assay. Alternatively, failure to detect emission light may be due to failure or deteriorated mechanical and/or electrical performance of an instrument (described below) for detecting the emission light.

Aspects of the invention are embodied in a method and apparatus for performing thermal melt analysis on the contents of receptacles that are processed through an instrument. For example, the apparatus may be incorporated as one of the modules of the analyzer 100. The method and apparatus may also be incorporated with real time and/or end point nucleic acid diagnostic assays.

Figure 4:
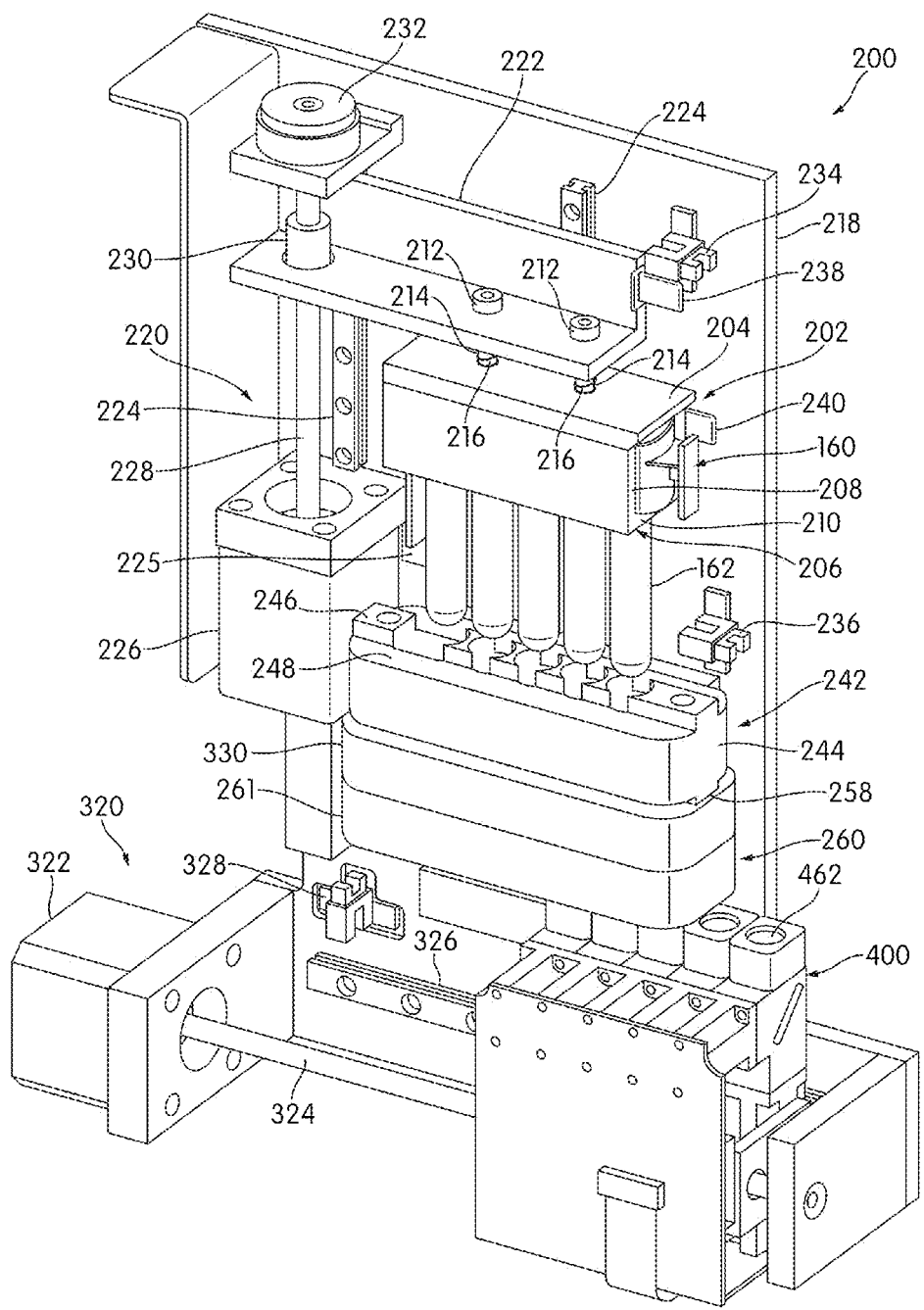
FIG. 4 is a perspective view of a thermal melt module embodying aspects of the present invention with a housing of the module omitted from the drawing so that internal components of the module can be seen.

A thermal melt module embodying aspects of the present invention is designated by reference number 200 in FIG. 4, which shows the internal components of the thermal melt module 200. In an embodiment of the module, the internal components are substantially enclosed by a housing that is omitted from FIG. 4 so that the internal components may be seen.

The thermal melt module 200 includes a receptacle holder 202 into which an MRD 160 can be inserted through an opening in the housing of the module 200. The receptacle holder 202 comprises cover 204 and a yoke 206 having substantially vertical sides 208 on both sides of the yoke 206 and lateral support flanges 210 extending along the bottom edges of the sides 208. When the MRD 160 is inserted into the receptacle holder 202, the connecting rib structure 164 of the MRD 160 is supported on the support flanges 210.

A vessel-receiving thermal assembly 242 receives the receptacle vessels 162 of the MRD 160 for heating the contents of each of the receptacle vessels 162 to a prescribed thermal melt temperature. The vessel-receiving thermal assembly 242 comprises a thermal block assembly 260 that is heated and applies thermal energy to the contents of the receptacle vessels 162 to heat the contents thereof and a vessel alignment block 244 disposed above the thermal block 260 and configured to align and position each of the receptacle vessels 162 with respect to the thermal block 260. More specifically as shown in FIGS. 5 to 10, the thermal block 260 comprises an interface block 330, a block element 261, and a bottom cover 286 secured to the block element 261. The block element 261 includes a plurality of receptacle holes 264 extending from a top surface 262 into the block 261. The number of receptacle holes 264 corresponds to the number of receptacle vessels 162 of the MRD 160—five in the illustrated embodiment. The block element 261 includes four threaded holes 266 formed in the respective corners of the block element 261. Interface block 330 includes openings 332 that correspond to and align with the receptacle holes 264 formed in the block element 261 and a slot 334 to accommodate a lower portion of the label-receiving structure 174 of the MRD 160 when the MRD is placed into the thermal block assembly 260. Interface block 330 may include through holes 336 formed in the corners of the block, and, in an exemplary embodiment, interface block 330 is secured to block element 261 by means of mechanical fasteners, such as screws or bolts, extending through the holes 336 into threaded holes 266 formed in the block element 261. In one embodiment, interface block 330 is made from aluminum or any other suitable, conducting metal, such as bronze, silver, steel, etc.

Figure 6:
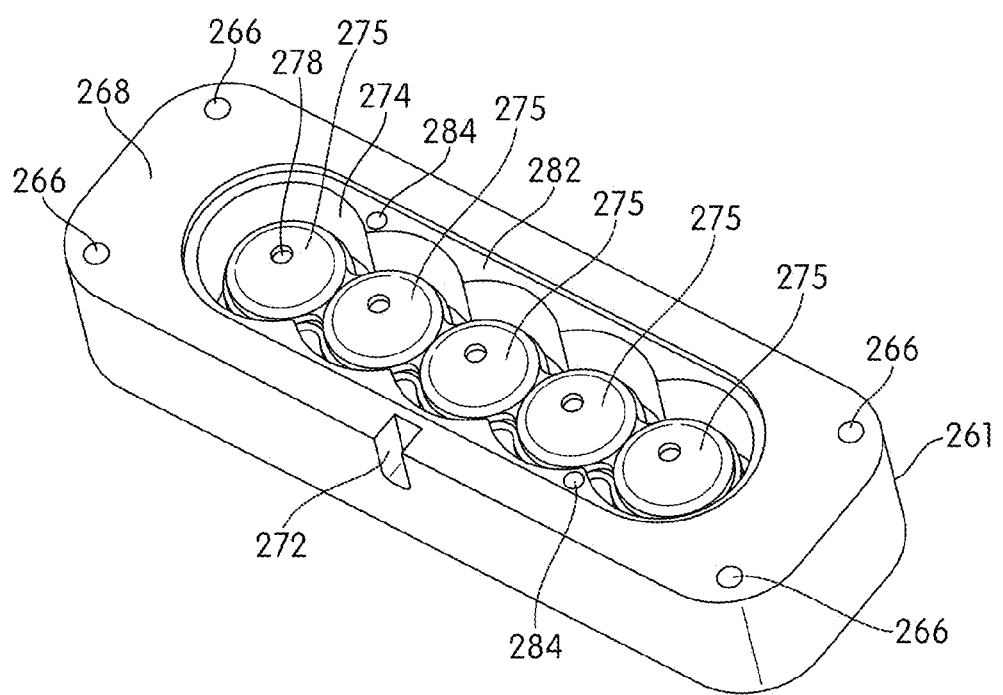
FIG. 6 is a bottom perspective view of a block element of the thermal block assembly.
Figure 7:
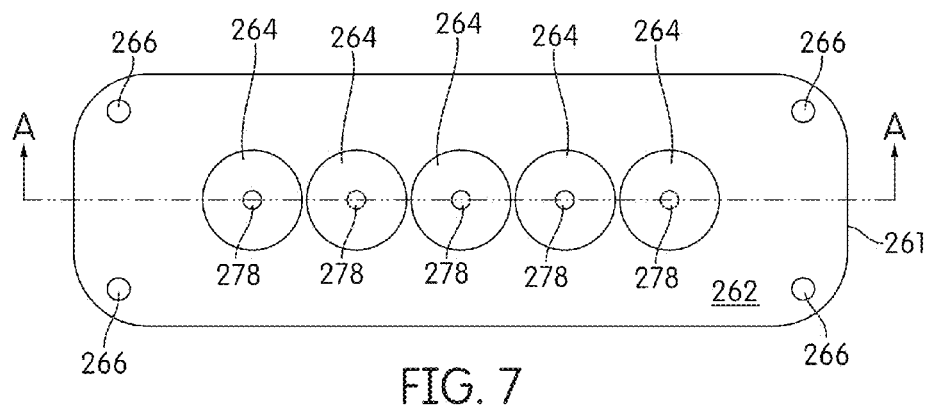
FIG. 7 is a top plan view of the block element.
Figure 8:
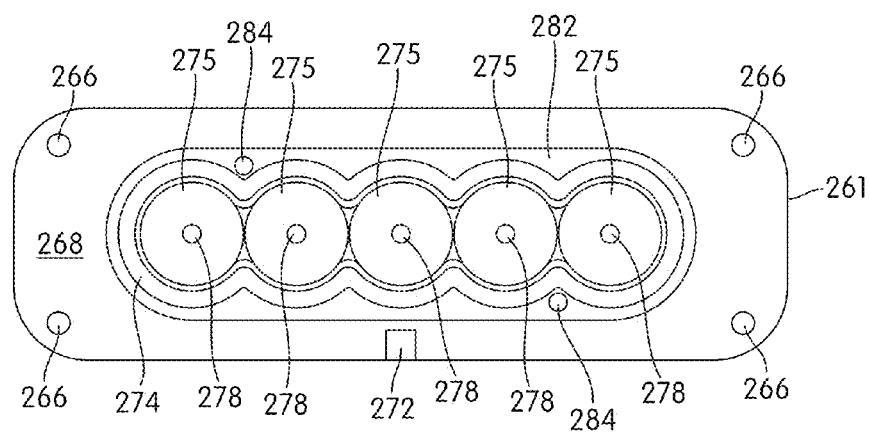
FIG. 8 is a bottom plan view of the block element.
Figure 9:
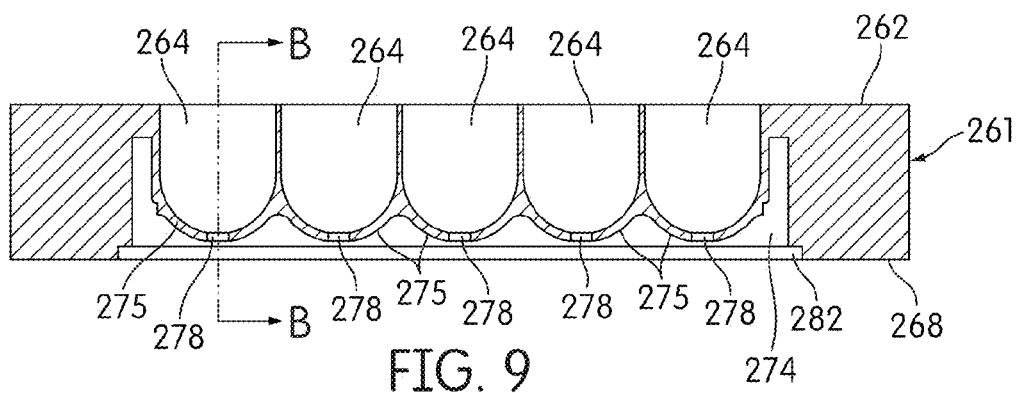
FIG. 9 is a longitudinal cross-section of the block element along the line A-A in FIG. 7.
Figure 10:
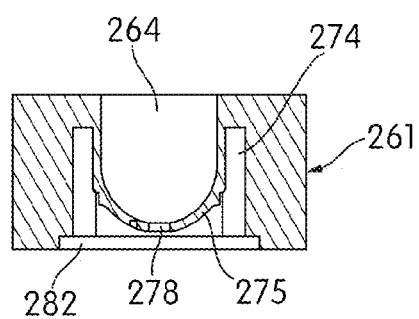
FIG. 10 is a transverse cross-section of the block element along the line B-B in FIG. 9.

Referring to FIGS. 6 and 8, which show a bottom surface 268 of the block element 261, block element 261 may include a recess 272 formed in one side of the block element 261 at a location substantially in the longitudinal middle of one side of the block element 261. Recess 272 may be provided to receive a thermistor for monitoring and controlling the temperature of the block element 261 and the thermal block assembly 260

Block element 261 further includes a hollowed-out portion 274 surrounding each receptacle hole 264 to define receptacle cups 275. In the illustrated embodiment, the receptacle cups 275 are interconnected at their respective laterally adjacent portions. In an alternative embodiment encompassed by the scope of the present invention, the block element 261 is substantially solid, except for the receptacle holes 264, and does not include a hollowed-out portion.

Each of the receptacle cups 275 has a centrally located signal hole 278 formed through the bottom of the cup. The signal holes 278 allow an emitted signal, such as a fluorescent emitted from the contents of a receptacle vessel 162 disposed within the receptacle hole 264, to be detected by an instrument located outside of the thermal block assembly 260. The signal holes 278 also allow an excitation signal such as light energy to be transmitted to the contents of a receptacle vessel 162 disposed within the receptacle hole 264 from outside the thermal block assembly 260.

Block element 261 is preferably formed from a material having high thermal conductivity and favorable machinability, such as 6061 aluminum. An aluminum thermal block 261 is preferably anodized. Because anodized aluminum itself may exhibit high fluorescence, the signal holes 278 and surrounding areas that are visible to an optical signal detector, such as the fluorometer described below, are preferably coated with a non-fluorescing material, such as Deep Space Black™ surface treatment from N-Science Corporation. Also, non-fluorescing black paint, dyes, or ink may be suitable to minimize or prevent background signals from the block element 261 entering the fluorometer.

Figure 5:
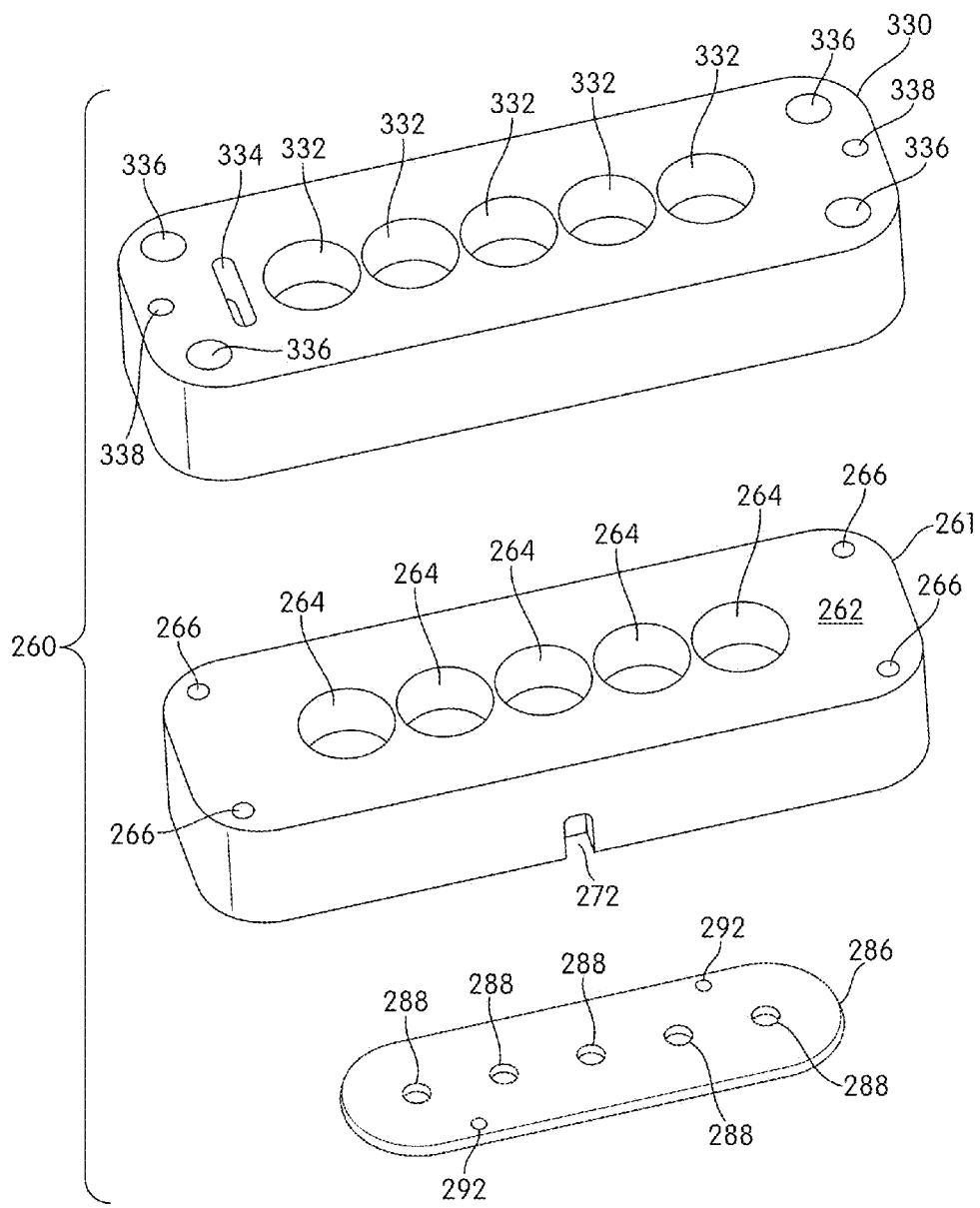
FIG. 5 is an exploded perspective view of thermal block assembly components of the thermal melt module.

Referring to FIG. 5, the bottom cover 286 is secured to the block element 261 in a shallow recess 282 (see FIGS. 8 to 10) formed in the thermal block 261 and having a shape conforming to the shape of the cover 286. Cover 286 is also preferably formed from a material having high thermal conductivity and favorable machinability, such as 6061 aluminum (preferably anodized), and is secured to the block element 261 by suitable means including mechanical fasteners, such as screws or bolts, extending through mounting through holes 292 formed in the bottom cover 286 into cover mounting holes 284 (see FIGS. 6 and 8) formed in the block element 261. Bottom cover 286 also preferably includes signal holes 288 that align with the signal holes 278 formed in the block element 261. As with the signal holes 278 of the block element 261, the signal holes 288 are preferably coated with a non-fluorescing material, such as Deep Space Black™ surface treatment from N-Science Corporation or non-fluorescing black paint, dyes, or ink, to minimize or prevent background signals from the bottom cover 286 entering the fluorometer Referring to FIGS. 11 to 12, the vessel alignment block 244 of the vessel-receiving thermal assembly 242 includes a raised center portion 246 extending longitudinally of the vessel alignment block 244 from one end to the opposite end of the alignment block 244. Raised portion 246 defines recessed shoulders 248 disposed along opposite sides of the raised center portion 246. These recessed shoulders 248 accommodate the support flanges 210 of the MRD holder 202 when the MRD holder 202 is lowered with respect to the vessel-receiving thermal assembly 242, such that the MRD 160 contacts the top surface of the raised portion 246 and the support flanges 210 do not contact the vessel alignment block 244. Vessel alignment block 244 further includes receptacle vessel guide holes 252, 254 extending through the vessel alignment block 244. Four of the guide holes 252 are substantially identical, circular holes configured to accommodate vessels 162 of the MRD, and the fifth guide hole 254 is elongated to accommodate the end vessel 162 of the MRD 160 and the label-receiving structure 174 of the MRD. In an alternate embodiment in which the MRD lacks a structure adjoining one or more of the receptacle vessels, such as the label-receiving structure 174, all of the guide holes of the vessel alignment block 244 may be identical in shape. The vessel alignment block 244 includes a number of guide holes corresponding to the number of receptacle vessels of the MRD. The vessel alignment block 244 also includes a plurality of lateral, threaded holes 256 (six in the illustrated embodiment) formed in one side of the vessel alignment block 244 by which the vessel alignment block 244 is secured to a wall 218 of the thermal melt module 220 by means of mechanical fasteners, such as screws or bolts.

Vessel alignment block 244 is preferably formed from a relatively non-heat conducting material having favorable machinability, such as Delrin®.

The vessel alignment block 244 is secured to the thermal block assembly 260 so that each of the receptacle vessel guide holes 252, 254 of the vessel alignment block 244 is aligned with a respective one of the openings 332 of the interface block 330 and a respective one of the receptacle holes 264 formed in the block element 261 of the thermal block assembly 260. Vessel alignment block 244 may be secured to the interface block 330 by means of mechanical fasteners, such as screws or bolts, inserted through holes 250 formed through the vessel alignment block 244 and into threaded holes 338 formed in the top surface of the interface block 330 (See FIG. 5). The vessel alignment block 244 includes a raised mounting block 258 (see FIGS. 11 and 12) on the bottom side of the block 244 at opposite longitudinal ends thereof. When the vessel alignment block 244 is secured to the thermal block assembly 260, only the mounting blocks 258 of the vessel alignment block 244 are in contact with the thermal block assembly 260, thereby providing a measure of thermal isolation between the vessel alignment block 244 and the thermal block assembly 260.

In one embodiment, each of the guide holes 252 has a diameter that is very close to, and only slightly larger than, the outside diameter of each receptacle vessel 162 so that each receptacle vessel 162 may slide through a corresponding guide hole 252 with little room for lateral play within the guide hole 252. The receptacle holes 264 of the thermal block assembly 260 have diameters that are somewhat larger than the diameters of the guide holes 252 of the vessel alignment block 244, and each receptacle hole 264 is coaxially aligned with a corresponding guide hole 252 and the corresponding openings 332 of the interface block 330. Accordingly, when a receptacle vessel 162 is inserted through a guide hole 252 of the vessel alignment block 244 and into an associated receptacle hole 264 of the thermal block assembly 260, the receptacle vessel 162 is precisely positioned with respect to the receptacle hole 264 by the guide hole 252 and openings 332 of the interface block 330 to centrally position the receptacle vessel 162 within the receptacle hole 264 with clearance between the outer surface of the receptacle vessel 162 and the inner surface of the receptacle hole 264 and preferably minimal, if any, contact between the receptacle vessel 162 and the thermal block assembly 260. The size of each of the receptacle holes 264 (diameter and depth) and the height of the receptacle alignment block 244 preferably provide a precise air gap surrounding the receptacle vessel 162 lowered into the receptacle hole 264.

Returning to FIG. 4, the thermal melt module 200 further includes a receptacle elevator 220 constructed and arranged to raise and lower the receptacle holder 202—and the MRD 160 carried thereby—relative to the vessel receiving assembly 242 to selectively place each of the receptacle vessels 162 of the MRD 160 into a respective one of the receptacle vessel guide holes 252, 254 of the vessel-alignment block 244 and a respective one of the receptacle holes 264 of the thermal block assembly 260.

The receptacle elevator 220 comprises a translating support bracket 222 that is supported relative to the wall 218 of the thermal melt module 220 on elevator guide tracks 224. A threaded shaft, or lead screw, 228 that is driven by an elevator motor 226 (which may comprise a stepper motor) is coupled to a screw follower 230 that is secured to the support bracket 222 so that powered rotation of the threaded shaft 228 by the elevator motor 226 causes corresponding up or down movement of the support bracket 222 on the elevator guide tracks 224.

In one embodiment, the receptacle holder 202 is secured to the support bracket 222 by isolation mounts 212 each of which comprises a pin or shaft 214 extending from the support bracket 222 through an opening in the cover 204 of the receptacle holder 202 and a shock-absorbing coil spring 216 coaxially surrounding the shaft 214 between the support bracket and the cover 204. When the receptacle holder 202 is lowered by the receptacle elevator 220 with respect to the vessel-receiving thermal assembly 242, the isolation mounts 212 absorb any shock caused as the receptacle holder 202 and/or the MRD come into contact with the vessel alignment block 244. Furthermore, the springs 216 of the isolation mounts 212 achieve a consistent and predictable force between the MRD 160 and the raised portion 246 of the vessel alignment block 244 as the support bracket 222 is lowered to a position such that the springs 216 are in a compressed condition.

In one embodiment, positioning of the MRD 160 relative to the vessel-receiving thermal assembly 242 is monitored and controlled by a system controller transmitting control signals to the receptacle elevator 220 (e.g., to the motor 226) and receiving receptacle position feedback signals. A system controller may comprise one or more programmable computers (stand alone and/or embedded), microprocessors, and/or microcontrollers and may be configured (e.g., programmed) to control one or more components or subsystems of the analyzer 100 or it may be configured to control the entire analyzer 100. In one embodiment, receptacle position feedback signals include the vertical position of the receptacle holder 202 and MRD 160 as determined by a receptacle-up sensor 234. Receptacle-up sensor 234 may comprise a slotted optical sensor attached to wall 218 and in communication with the system controller. Sensor 234 is tripped by a sensor tab attached to some portion of the receptacle elevator 220—such as a support bracket sensor tab 238 extending from the support bracket 222—when the receptacle holder 202 has been moved to the raised position by the receptacle elevator 220. Other types of sensors, such as proximity switches, contact switches, or magnetic switches, may also be used. The position of the receptacle holder 202 may also be determined by a receptacle-down sensor 236, which may also comprise a slotted optical sensor attached to wall 218 and in communication with the system controller. Sensor 236 is tripped by a sensor tab attached to some portion of the receptacle elevator 220—such as an receptacle holder sensor tab 240 attached to the receptacle holder 202—to indicate that the receptacle holder 202 has been moved to a lowered position by the receptacle elevator 220. Other types of sensors, such as proximity switches, contact switches, or magnetic switches, may also be used. Between the raised and lowered positions, the position of the receptacle holder 202 can be monitored by means of a rotational encoder 232 coupled to the threaded shaft 228. The combination of sensors 234 and 236 and rotational encoder 232, along with the system controller, provide accurate process controls to ensure the MRD 160 is properly inserted into vessel-receiving thermal assembly 242.

In an alternate embodiment, the receptacle holder 202 and the MRD 160 are held in a fixed position, and the thermal block assembly 260 is moved relative to the receptacle holder 202 to place the receptacle vessels 162 into the receptacle vessel guide holes 252, 254 of the vessel-alignment block 244 and the receptacle holes 264 of the thermal block assembly 260.

The thermal melt module 200 further includes a signal-detecting device 400, such as a fluorometer disposed beneath the vessel-receiving thermal assembly 242. Details of an embodiment of the signal detector 400 are described below. In the illustrated embodiment, the signal detector 400 includes a number of signal-receiving channels corresponding to the number of receptacle vessels 162 of the MRD 160. The signal-detecting device 400 is often configured such that each signal-receiving channel in the signal-detecting device 400 corresponds to a different excitation and emission signal and thus is configured to detect a fluorescent signal corresponding to a unique dye. The signal detector 400 is positionable with respect to the vessel-receiving thermal assembly 242 so that one or more detection openings 462 of the signal detector 400—each corresponding to a different signal-receiving channel—may be aligned with the signal holes 288, 278 of the thermal block assembly 260 to direct an excitation signal toward the contents of and detect a fluorescent emission from the contents of a receptacle vessel 162 that is lowered into the receptacle hole 264 of the thermal block assembly 260.

In the illustrated embodiment, the thermal melt module 200 includes a detector translating mechanism 320 configured to move the signal detector 400 with respect to the vessel-receiving thermal assembly 242 to selectively align detection openings 462 of the signal detector 400 with different signal holes 278, 288 of the thermal block assembly 260. The detector translating mechanism 320 includes a motor 322, which may comprise a stepper motor, operatively coupled to a threaded shaft, or lead screw 324 that is coupled to a screw follower (not shown) that is secured to the signal detector 400 which is translatably supported on a guiderail 326 so that powered rotation of the threaded shaft 324 by the motor 322 causes lateral, linear translation of the signal detector 400 with respect to the vessel-receiving thermal assembly 242.

In one embodiment, positioning of the signal detector 400 is monitored and controlled by a system controller transmitting control signals to the detector translating mechanism 320 (e.g., to the motor 322) and receiving detector position feedback signals. The position of the signal detector 400 at one end of the guiderail 326 may be confirmed by means of a sensor 328, such as a slotted optical sensor attached to wall 218, that detects a sensor tab (not shown) secured to the signal detector 400. Other types of sensors, such as proximity switches, contact switches, or magnetic switches, may also be used. A similar sensor may be provided at an opposite end of the guiderail 326. In addition, a rotational encoder may be coupled to the threaded shaft for monitoring the position of the signal detector 400. The position sensor(s) and rotational encoder, along with the system controller, provides monitoring and control of the position of the signal detector 400.

The thermal block assembly 260 is heated by a heating element, e.g., a resistive foil (not shown) (e.g., OMEGA Engineering, Inc. (Stamford, Conn.) Part Number KHLV-105/10-P), attached to the thermal block assembly 260 by means of adhesive and controlled by a controller that transmits power signals to the heating element. The temperature of the thermal block assembly 260 is monitored by a temperature sensor embedded in the thermal block assembly 260, e.g., in recess 272. The temperature sensor is in communication with the heating element, via a controller, to provide temperature feedback signals that provide input for a temperature control algorithm that controls power signals transmitted to the heating element. The heating element, the temperature sensor, the controller, and the temperature control algorithm comprise a thermal block temperature control system. Rather than ramping the temperature—ether linearly or in step-wise fashion—from an initial temperature to a final temperature and then cooling the temperature back to the initial temperature, while in operation the thermal block assembly 260 is maintained at a steady state temperature that is higher than the temperature of the contents of the MRD 160 when the MRD is first placed into the module 200. The temperature of the contents of the MRD placed in thermal contact with the heated thermal block assembly 260 will follow an increasing temperature vs. time trajectory.

When the receptacle vessels 162 are first lowered into the receptacle openings 264 of the thermal block assembly 260, the initial temperature differential between the receptacle vessels 162 and the thermal block assembly 260 can cause a transitory change in the temperature of the thermal block assembly 260. The thermal block temperature control system, receiving temperature signals from the temperature sensor embedded in the thermal block assembly 260, would normally generate and transmit power signals to the heating element in an attempt to regulate the temperature of the thermal block assembly 260. To modulate the effect of the temperature differential between the receptacle vessels 162 and the thermal block assembly 260—and thereby maintain the stability of the thermal block temperature control system—the hollowed-out portion 274 of the thermal block 261 acts as a buffer, or filter, between the portions of the thermal block 261 that are in close proximity to the receptacle vessels 162 and a portion of the block 261 in which the temperature sensor is embedded. The air within the hollowed-out portion 274 diminishes thermal conductivity across the thermal block assembly 260, and thus the full magnitude of the transitory temperature changes near the receptacle openings 264 when the receptacle vessels 162 are first inserted into the openings is not detected at the temperature sensor, thereby modulating temperature changes detected by the temperature sensor.

The temperature of the contents of the receptacles will, within a level of precision, follow a predictable, exponential temperature vs. time trajectory between the initial temperature of the contents when the receptacle vessels 162 are first lowered into the thermal block assembly 260 and the temperature of the thermal block assembly. The level of precision, i.e., the variation from an expected temperature vs. time trajectory, will depend on various parameters and tolerances within the system, such as, the initial temperature of the contents of the receptacle vessels 162, ambient temperature, the volume and specific heat of the fluid contents within the receptacle vessel 162, the size of the air gap between each receptacle vessel 162 and the thermal block assembly 260, and the type of material and thickness of the walls of the receptacle vessel 162. As the MRD's 160 are preferably made from the same material, the specific heat of each MRD 160 should be known and constant, but the thickness of the receptacle vessel walls may vary in accordance with applicable manufacturing tolerances. By controlling and minimizing these tolerances, the temperature vs. time trajectory becomes more precise and repeatable. Variability in the initial temperature of the contents of the receptacle vessel, may, in certain embodiments, be controlled by the precision of the temperature of the incubator (e.g., incubator 112, 114, or 116 (see FIG. 1)) from which the MRD 160 is removed prior to placing the MRD 160 into the thermal melt module 200 and the time required to move the MRD from the incubator to the thermal melt module 200 and lower the receptacle vessels 162 into the thermal block assembly 260. Variability in the volume of the contents of each receptacle vessel 162 can be controlled by the precision of the fluid transfer apparatus(es) employed and the precision of fluid dispense verification systems, if any, that are employed. Variability in the size of the air gap between each receptacle vessel 162 and the thermal block assembly 260 and variability in the thickness of the walls of the receptacle vessel 162 can be controlled by the precision of the manufacturing of the thermal block assembly 260 and the precision of the manufacturing of the MRD 160.

Measuring the temperature of the fluid contents of the receptacle vessel 162 can itself introduce further variability to the system. Because a temperature sensor itself has thermal mass, it has a thermal time constant that can affect the correspondence between the temperature indicated by the sensor and the actual temperature of the liquid. Because of this, the temperature sensor (indicated temperature) will lag the actual fluid temperature if that fluid is being heated or cooled.

Figure 17:
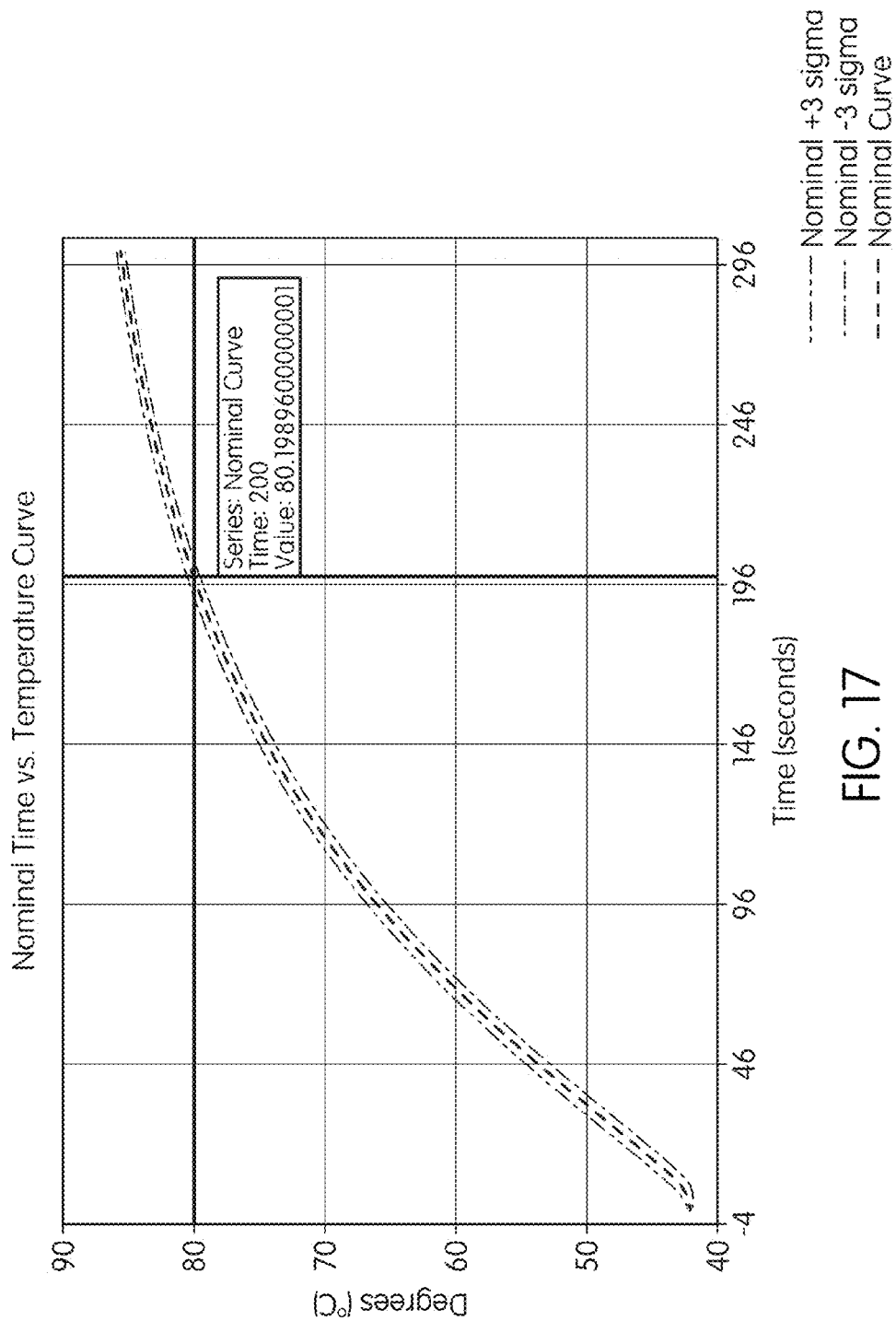
FIG. 17 is an exemplary time vs. temperature calibration curve.

In embodiments where the temperature of the contents of the receptacles (e.g., MRDs) is not actively monitored during the melt, these and other sources of variability are accounted for by the generation of one or more calibration time vs. temperature curve(s). See FIG. 17. Calibration curves provide a guide for the operator of the module to determine the temperature of the contents of the receptacles based on how long the receptacles have been present within the melt station. These curves can be generated by a variety of different methods. For example, temperature sensors (e.g., thermistors) can be incorporated in a fluid within the receptacles. Once these receptacles are introduced to the module 200, the fluid temperature is actively monitored via the temperature sensors to follow the temperature rise of the fluid over time. Repeating this process multiple times can provide sufficient data to generate a calibration curve for the module 200 to determine the temperature of the fluid within the receptacle based on how long the receptacle has been in the module 200. As these data will inherently contain a level of variability, this variability, e.g., 1%, 2%, 3%, 4%, 5%, or another level of variability, is accounted for in the calibration curve as a percentage deviation from the nominal curve. FIG. 17 shows a deviation of plus and minus 3 percent from the nominal curve.

Since thermistors have particular thermal time constants, these thermistors may provide a delayed indication of the reaction fluid temperature. So, another frequently preferred method of generating the calibration curve is by plotting time vs. multiple calibrators that are known to melt at a specific temperature across the operable melt range. In such embodiments a real-time indication of the temperature of the contents of the receptacles at any particular time can be identified based on when each calibrator melts, causing the generation of a detectable signal. Once the calibration time vs. temperature curve is generated it can be referenced to accurately plot fluorescence data on a temperature scale.

One of skill in the art would appreciate that the master curve generated for one particular station may not be applicable to another station due to potential variabilities in the system. In addition, different sample volumes or sample types will often require specific master curves. These curves will account for additional variability in the system, e.g., receptacle materials, air gaps, initial temperatures, etc.

The data recorded by the signal detector 400 in one embodiment is a fluorescence (relative fluorescence unit or "RFU") vs. time signal. The fluorescence vs. time signal data is analyzed to determine the melt temperature, for example, by reference to a time vs. temperature calibration curve. In one embodiment, the temperature derivative of the fluorescence vs. time signal data is analyzed to identify a spike that is indicative of the melt temperature. The melt temperature thus determined is compared to melt temperatures from the predetermined calibration curves for specific nucleic acid targets to infer the nucleic acid target that is present in the sample that produced a like melt temperature. That is, in one embodiment, the module 200 is calibrated against a standard set of double stranded or hairpin oligonucleotides or polynucleotides with known melt temperatures—e.g., as determined by a standardized device, such as the Qiagen Rotor-Gene 6000—spanning the temperature range of interest. Ideally, the fluid temperature in each receptacle vessel 162 is consistent from receptacle to receptacle and is repeatable from test to test. If the fluid temperature is found to be consistent and repeatable, a single calibration curve can be used for the entire MRD 160. On the other hand, if there is significant receptacle to receptacle temperature variability it may be preferable to apply separate calibration curves for each receptacle vessel 162.

As noted above, in practice there is a chance that the timing of transferring the MRD 160 from the incubator to the module 200 may vary (among other variabilities noted above), which may have an effect on the temperature of the sample in the receptacle. If this temperature varies from an expected temperature, placement of the actual temperature of the sample on the time scale (using the calibration curve) will be altered. For example, if the sample is colder than expected it will take longer than expected for the sample to heat, so that at any particular time after placement of the MRD 160 in the module 200 the temperature of the sample will be lower than expected. One solution to this source of potential variability involves the use of one or more calibrators having a known melt temperature (e.g., a molecular beacon) in the sample. Often, two or more calibrators are utilized, each having a different and known melt temperature.

At the known temperature the bonds holding the self-hybridized beacon in its hairpin shape are broken, which results in the separation of the fluorophore and quencher moieties attached to the beacon (the fluorophore may fluoresce at the same or different wavelength than any fluorophores attributable to the test sample). Due to this separation, the fluorescence of the fluorophore becomes detectable since it is no longer being quenched. At the point when the calibrator becomes detectable, the temperature of the sample will be known. Often, a particular time that the calibrator will become detectable after the MRD is placed within the module is expected based on the calibration curve. When the calibrator becomes detectable at a time that differs from the expected time, reference to the calibration curve will permit one to accurately adjust the temperature trajectory of the sample to accurately compare sample temperature with fluorescence measurements. Often this results in shifting the RFU vs. temperature curve along the temperature axis to plot the melt curve accurately based on the actual temperature of the sample.

Though they are not necessary to effectively practice the present methods, such calibrators often eliminate the need to actively monitor the temperature of the sample contained in the receptacle vessel. Such calibrators may be advantageous when, for example, different sample types, different ambient temperatures, different sample volumes, different receptacle vessel materials, different receptacle vessel wall thicknesses, different air gaps between the receptacle vessel and the heat source, and/or other sources of inter- or intra-sample variability are present to appropriately place individual melt profiles on a pre-determined, concurrently determined, or otherwise known melt curve.

In the presence of sufficient confidence in the precision and repeatability of the temperature response of the fluid contents of the receptacle vessel 162, it may become unnecessary to measure the temperature of the receptacle vessel 162 or the receptacle vessel 162 contents. In such circumstances, fluorescence vs. time data may be recorded for the sample and compared to fluorescence vs. time curves for known genotypes.

Figure 13:
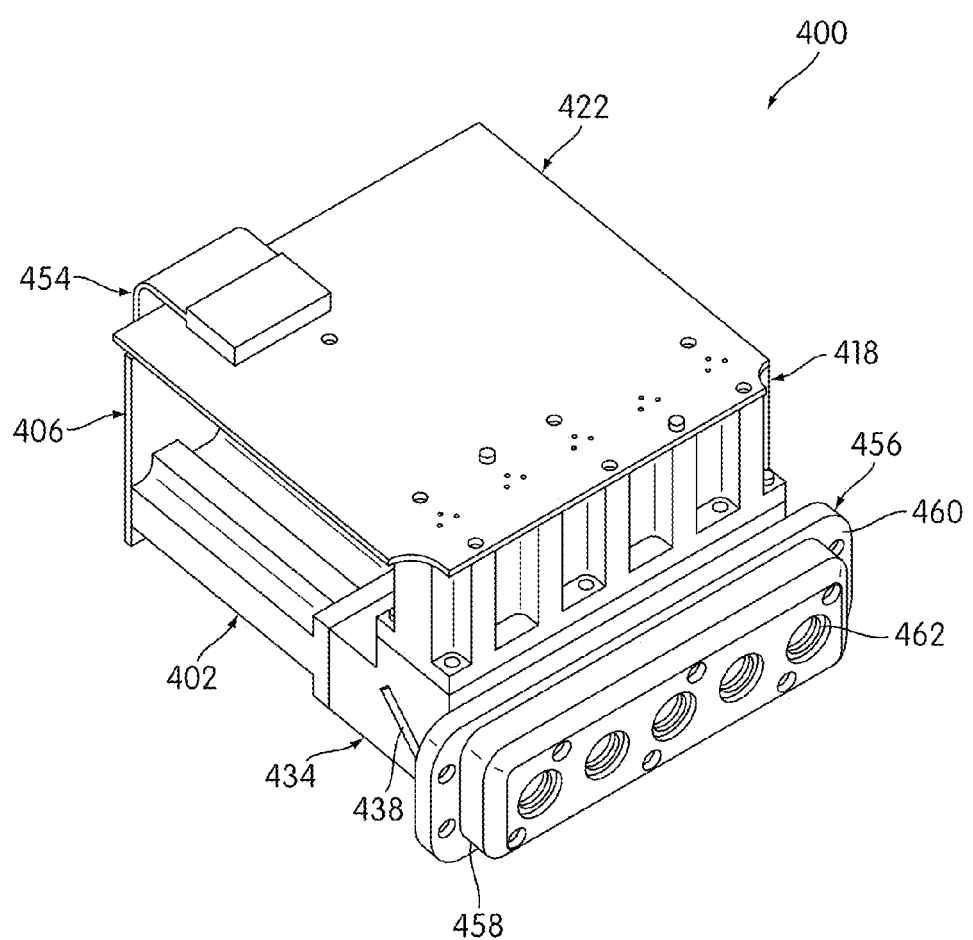
FIG. 13 is a perspective view of a signal detector for use in conjunction with the present invention.

The present invention is not bound to the use of any particular excitation source or emission detector, or configuration thereof. An exemplary signal detector 400 for use in conjunction with the present invention is shown in FIG. 13. As shown in FIG. 13, which is a perspective view of a signal detector, the detector 400 includes a housing that comprises a detector housing 418 and an excitation housing 402, both connected at a right angle with respect to each other to a lens and filter, or optics, housing 434. Each of the housing components 402, 418 and 434 may be made from, for example, machined aluminum and secured to one another by suitable fasteners, such as screws, and is preferably anodized. An excitation printed circuit board ("PCB") 406 is connected to an end of the excitation housing 402, and a detector PCB 422 is connected to an end of the detector housing 418. A flexible cable 454 connects the excitation PCB 406 with the detector PCB 422. Details of such an exemplary signal detector are described in previously-incorporated U.S. Patent Application Publication No. US20120221252.

In one embodiment, the signal detector comprises a fluorometer configured to excite a fluorescent dye of a specific wavelength (i.e., color), by directing an optical excitation signal of a specified, associated excitation wavelength at a receptacle containing a sample with which the fluorescent dye is mixed, and to detect an emission signal having a wavelength corresponding to the wavelength, or color, of the specific dye. Different fluorescent dyes are excited at different wavelengths. In one multiplex application of the present invention, suitable dyes include the rhodamine dyes tetramethyl-6-rhodamine ("TAMRA") and tetrapropano-6-carboxyrhodamine ("ROX") and the fluorescein dyes 6-carboxyfluorescein ("FAM") and, each in combination with a DABCYL quencher. Other suitable dyes include, for example, 5'-hexachlorofluorescein phosphoramidite ("HEX"), and 2',7'-dimethoxy-4',5'-dichloro-6-carboxyfluorescein ("JOE"), BIOSEARCH BLUE® (BG5-5088), CAL FLUOR® Gold 540, CAL FLUOR® Orange 560, CAL FLUOR® Red 590, CAL FLUOR® Red 610, CAL FLUOR® Red 635, PULSAR® 650, Quasar 670, Quasar 705, among others. Because preferred dyes are excited at different wavelengths, each signal detector 400 is preferably tailored to emit an excitation light at or near the desired excitation wavelength (i.e., color) for the particular dye that the fluorometer is intended to detect. Accordingly, component selection for the detector/fluorometer will, in many instances, be governed by the particular dye for which the signal detector 400 is intended.

Thermal Melt Analysis

Figure 14:
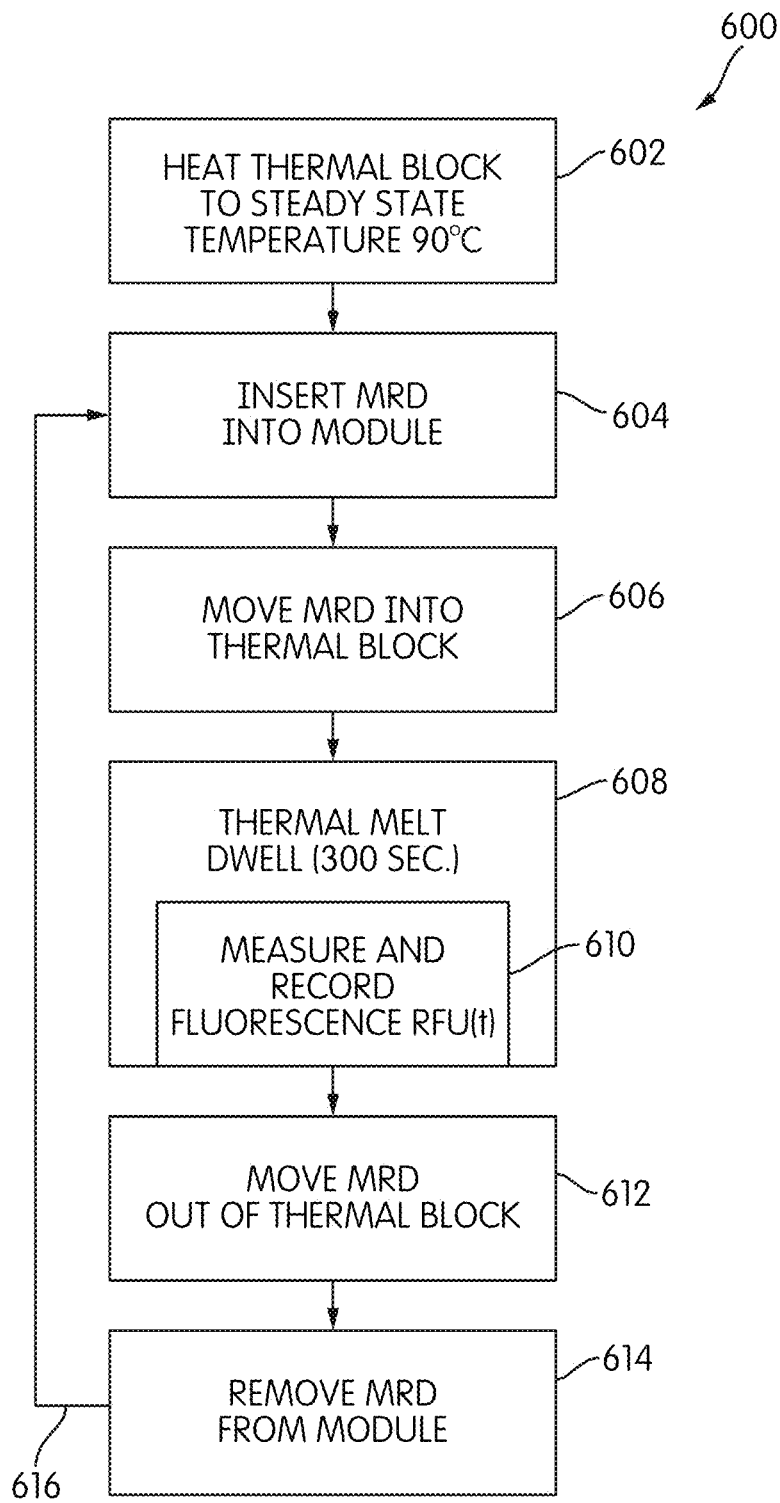
FIG. 14 is a flow chart showing the steps of an exemplary thermal melt analysis procedure.

An exemplary thermal melt analysis process 600 is represented by a flow chart in FIG. 14. To perform thermal melt analysis, in one embodiment, at step 602, the thermal block assembly 260 is heated to a steady state high temperature of, for example, 90° C. The temperature of the thermal block assembly can be measured by the temperature sensor embedded into the thermal block assembly 260. In step 604, an MRD 160 is inserted into the receptacle holder 202 of the thermal melt module 200 by a receptacle transport mechanism under the control of a system controller. In step 606, the receptacle vessels 162 of the MRD 160 carried in the receptacle holder 202 are lowered by the receptacle elevator 220 into the vessel-receiving thermal assembly 242 so that the lower ends of the vessels 162, in which the contents are held, are disposed in the receptacle holes 264 of the thermal block assembly 260. In one embodiment, an MRD detection sensor 225 (See FIG. 4) is provided within the thermal melt module 200 to detect the presence of an MRD inserted into the MRD holder 202. The sensor 225, which may comprise, e.g., any type of presence sensor/switch, such as, optical, mechanical, magnetic, capacitive, may be attached to wall 218 at a location near the end of the MRD holder 202 opposite the end at which the MRD is inserted into the holder to detect when the MRD has been fully inserted into the MRD holder 202. Upon receipt by the system controller of a signal from the MRD detection sensor 225, the system controller generates a command for the receptacle elevator 220 to automatically lower the MRD 160 into the vessel-receiving thermal assembly 242.

In step 608, the receptacle vessels 162 of the MRD 160 dwell within the thermal block assembly 260 to thereby raise the temperature of the contents of the receptacle vessels 162. In one example, the receptacle vessels 162 are retained within the thermal block assembly 260 for a dwell time empirically determined to be sufficient for the contents of the receptacle vessels 162 to reach a temperature that is above (e.g., by up to a few degrees C.) the expected melt temperature, such as 300 sec. (5 minutes). Though not wishing to be bound by any particular theory, the temperature of the liquid contents of each of the receptacle vessels 162 rises, in an inverse exponential manner, towards the temperature of the heated thermal block assembly 260.

In one embodiment, the initial temperature of the contents of the receptacle vessels 162 is approximately 42° C. when the receptacle vessels 162 are first lowered into the thermal block assembly 260. In other embodiments, the time required to perform the thermal melt analysis can be reduced by first pre-heating the receptacle contents prior to lowering the receptacle vessels 162 into the thermal block assembly 260. Care should be taken, however, to avoid pre-heating the contents of the receptacle vessel 162 to a temperature that approaches a temperature approximating a melting temperature for a hybridized oligonucleotide or polynucleotide having low G/C content and containing mismatches.

Figure 16:
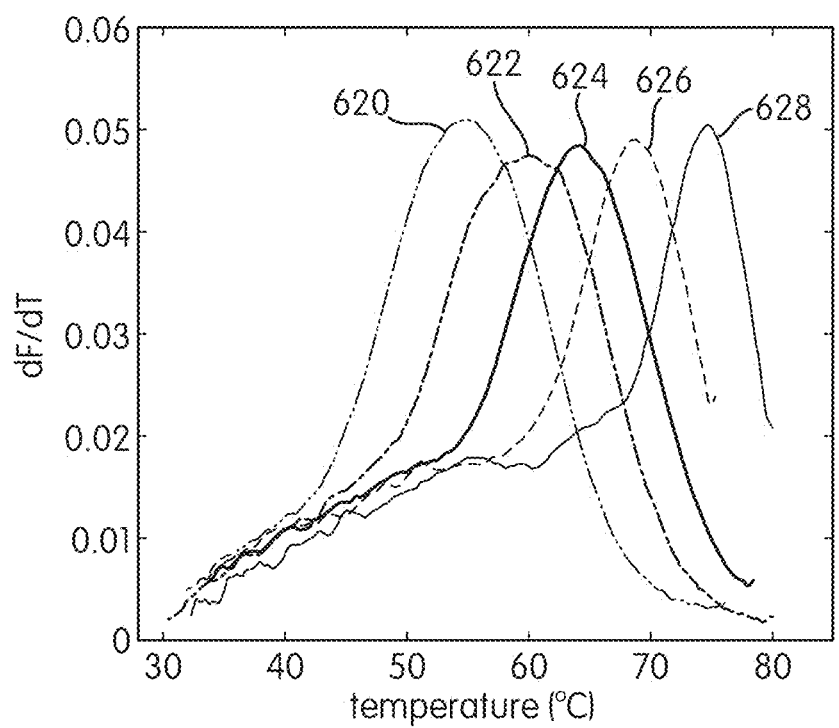
FIG. 16 is a plot of the derivatives of fluorescence signals with respect to temperature for five different fluorescent signals.

In one embodiment, simultaneously with step 608, in step 610, the signal detector 400 measures and records the fluorescence, RFU(t), of the fluorophore or fluorophores in the liquid contents of each of the receptacle 162 as the temperature rises. To detect multiple melt temperatures within a single sample, requires multiple fluorescent colors (dyes) (1 color for each melt temperature). FIG. 16 shows a plot of the derivatives of five different fluorescent signals with respect to temperature vs. temperature, as represented by plots 620, 622, 624, 626, 628. Each different plot, or line, represents a different fluorescent signal (color). The peak of each line represent an inflection point at which the change in fluorescence with respect to temperature changed from positive to negative—thereby indicating a thermal melt temperature. In one embodiment, each channel of the signal detector corresponds to a different fluorescent colors, and therefore, the signal detector is indexed by the translating mechanism 320 to sequentially place each signal-receiving channel into an operative position with respect to each receptacle vessel 162 of the MRD 160. In one embodiment, the signal detector 400 is indexed at a rate of one channel every 0.25 seconds, and a signal measurement is taken every 0.125 seconds. The different, discrete signal measurements are compiled into different melt curves, each corresponding to a different fluorescent color. In an alternative embodiment in which each channel of the signal detector 400 is configured to measure different fluorescent signals, it may not be necessary to index the signal detector 400 with respect to the MRD 160.

If the melt temperatures are far enough apart from one another, a single fluorescent color could be used to detect all melt temperatures. The single resulting melt curve would have multiple inflection points, each corresponding to a different thermal melt temperature.

Accounting for and/or minimizing receptacle-to-receptacle temperature variation and intra-receptacle temperature variation is an important aspect of the present apparatus and methods to maintain a consistent and high overall accuracy for melt analyses of multiple samples. This is important since the temperature of the heat source is constant, while the sample temperature rises. Factors affecting heat transfer from the heat source to the sample such as receptacle vessel materials, receptacle vessel material thickness, air gaps between each receptacle vessel and each receptacle hole, sample type, sample volume, among other factors, are important to evaluate.

In one embodiment involving the concurrent thermal melt analysis of multiple samples, each sample is contained in a receptacle vessel comprising the same material, and having the same or substantially the same wall thickness, as each other concurrently analyzed sample. In another related embodiment the sample volume contained in each of the multiple samples is the same or substantially the same.

One preferred embodiment of reducing receptacle-to-receptacle and intra-receptacle temperature variation involves reducing the position variability of each receptacle vessel 162 relative to the heated thermal block 261 when the receptacle vessels 162 are positioned within the heated thermal block 261. For example, in one embodiment a predefined air gap is formed between the inner surface of each receptacle hole 264 and each receptacle vessel 162. This predefined air gap is generally defined by the distance between each receptacle vessel 162 and the inner surface of each receptacle hole 264. As the present invention is not limited to any specific geometric orientation of the receptacle hole 264 or receptacle vessel, the air gap may be defined by the distance between one or more particular point(s) on the inner surface of each receptacle hole 264 and one or more corresponding particular point(s) on the outer surface of each receptacle vessel 162. In certain embodiments the air gap is zero "0," meaning there is no air gap between one or more particular point(s) on the inner surface of each receptacle hole 264 and the corresponding one or more particular point(s) on the outer surface of each receptacle vessel 162. In certain other embodiments the air gap is varied (i.e., defined by a varying distance) between the one or more particular point(s) on the inner surface of each receptacle hole 264 and the corresponding one or more particular point(s) on the outer surface of each receptacle vessel 162. In additional embodiments the air gap is consistent (i.e., defined by a consistent distance) between the one or more particular point(s) on the inner surface of each receptacle hole 264 and the corresponding one or more particular point(s) on the outer surface of each receptacle vessel 162.

In step 612, the receptacle vessels 162 of the MRD 160 carried in the receptacle holder 202 are raised by the receptacle elevator 220 out of the vessel-receiving thermal assembly 242. In step 614, the MRD 160 is removed from the receptacle holder 202 of the thermal melt station 200. Steps 604 through 614 can then be repeated for each subsequent MRD 160 within which thermal melt is performed. Frequently, the steps encompassed by 616 are accomplished within about 5 minutes, within about 4 minutes, within about 3 minutes, within about 2 minutes, or within about 1 minute. Most frequently, the steps encompassed by 616 are accomplished within about 5 minutes or less.

Figure 15:
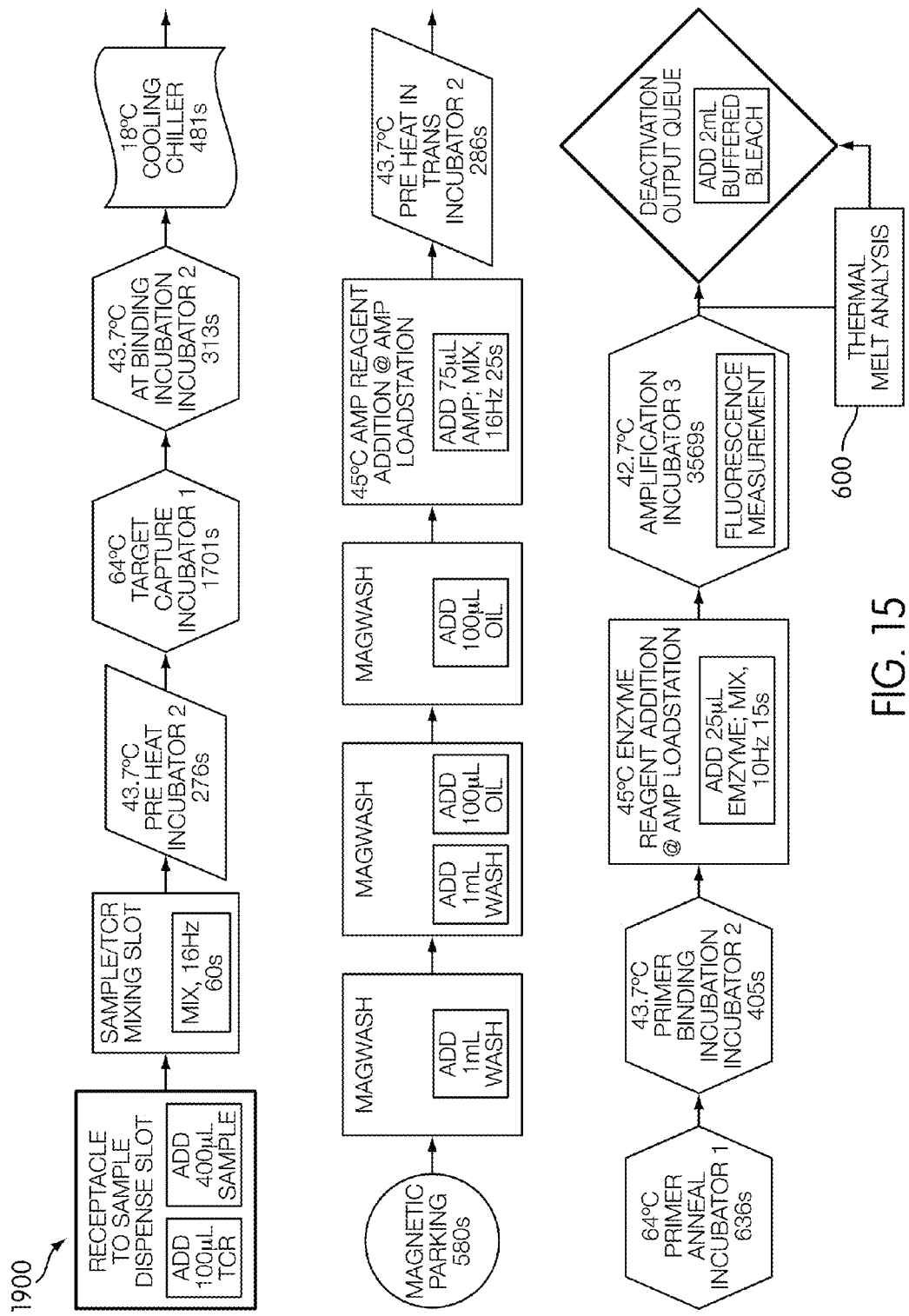
FIG. 15 is a flow chart showing the protocols of an exemplary real-time amplification assay.

The process steps of an exemplary nucleic acid diagnostic procedure 1900 are illustrated in the flow chart shown in FIG. 15. The procedure 1900 may be performed by a diagnostic analyzer 100 of which one or more incubators, such as incubators 112, 114, and/or 116 and thermal melt module 200 are components and which is controlled by the system controller executing software that includes an algorithm embodying procedure 1900 encoded or stored on a computer-readable medium. The process shown in FIG. 15 is described in detail in previously-incorporated U.S. patent application Ser. No. 13/404,437. The steps described represent exemplary TAA procedures only. Persons of ordinary skill will recognize that the steps described below may be varied or omitted or that other steps may be added or substituted in accordance with other amplification assay procedures, including isothermal- and/or temperature cycling-dependent amplification assays, now known or yet to be developed. Reagent formulations for performing a host of amplification procedures are well known in the art and could be used in or readily adapted for use in the present invention. See, e.g., Kacian et al., U.S. Pat. No. 5,399,491; Becker et al., U.S. Pat. No. 7,374,885; Linnen et al., "Compositions and Methods for Detecting West Nile Virus," U.S. Pat. No. 7,115,374; Weisburg et al., "Compositions, Methods and Kits for Determining the Presence of *Trichomonas Vaginalis* in a Test Sample," U.S. Pat. No. 7,381,811; and Kacian, "Methods for Determining the Presence of SARS Coronavirus in a Sample," U.S. Patent Application Publication No. 2010-0279276 A1, the respective disclosures of which are hereby incorporated by reference.

Following the amplification, in the exemplary process steps depicted in FIG. 15, the MRD 160 may be moved to a thermal melt module 200 to perform a thermal melt analysis step 600, such as described above and shown in FIG. 14.

After the nucleic acid-based assay, including the thermal melt, is complete, and to avoid possible contamination of subsequent amplification reactions, the reaction mixture can be treated with a deactivating reagent that destroys nucleic acids and related amplification products in the reaction vessel. In such an example, after amplification and real-time measurements, in step 1952, the receptacle is moved to a deactivation queue, or module (not shown), and, in step 1954, 2 mL of a bleach-based agent are provided to each receptacle to deactivate nucleic acid (i.e., alter the nucleic acid such that it is non-amplifiable) present in the receptacle. Such deactivating agents can include oxidants, reductants and reactive chemicals, among others, which modify the primary chemical structure of a nucleic acid. These reagents operate by rendering nucleic acids inert towards an amplification reaction, whether the nucleic acid is RNA or DNA. Examples of such chemical agents include solutions of sodium hypochlorite (bleach), solutions of potassium permanganate, formic acid, hydrazine, dimethyl sulfate and similar compounds. More details of a deactivation protocol can be found in, e.g., Dattagupta et al., U.S. Pat. No. 5,612,200, and Nelson et al., U.S. Patent Application Publication No. US 2005-0202491 A1, the respective disclosures of which are hereby incorporated by reference.

Hardware and Software

Aspects of the invention are implemented via control and computing hardware components, user-created software, data input components, and data output components. Hardware components include computing and control modules (e.g., system controller(s)), such as microprocessors and computers, configured to effect computational and/or control steps by receiving one or more input values, executing one or more algorithms stored on non-transitory machine-readable media (e.g., software) that provide instruction for manipulating or otherwise acting on the input values, and output one or more output values. Such outputs may be displayed or otherwise indicated to a user for providing information to the user, for example information as to the status of the instrument or a process being performed thereby, or such outputs may comprise inputs to other processes and/or control algorithms. Data input components comprise elements by which data is input for use by the control and computing hardware components. Such data inputs may comprise positions sensors, motor encoders, as well as manual input elements, such as keyboards, touch screens, microphones, switches, manually-operated scanners, etc. Data output components may comprises hard drives or other storage media, monitors, printers, indicator lights, or audible signal elements (e.g., buzzer, horn, bell, etc).

Software comprises instructions stored on non-transitory computer-readable media which, when executed by the control and computing hardware, cause the control and computing hardware to perform one or more automated or semi-automated processes.

EXAMPLES

The following examples are provided in order to demonstrate and further illustrate certain embodiments and aspects of the present disclosure and are not intended to be construed as limiting the scope thereof.

Example 1

Figure 18:
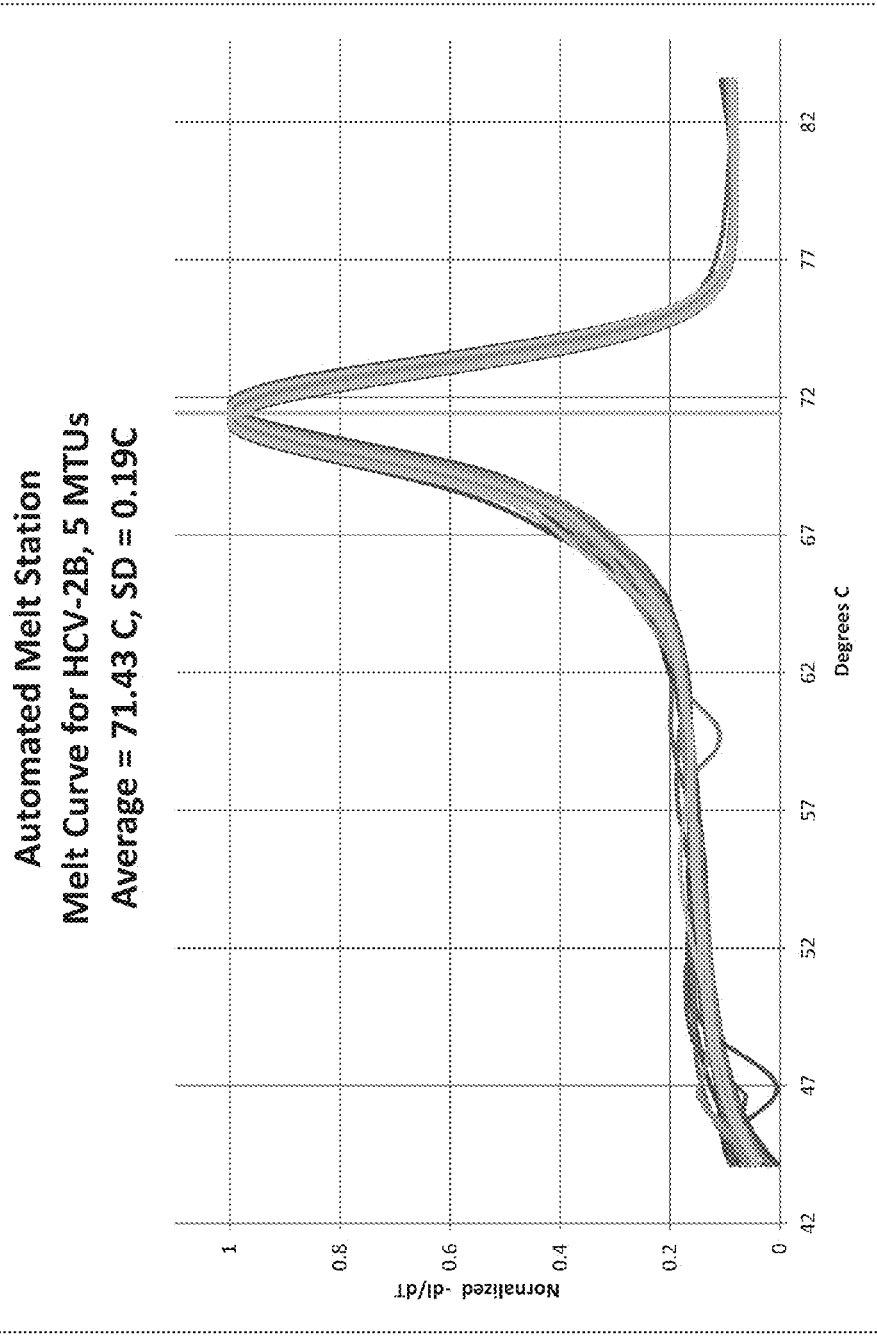
FIG. 18 is a plot of the derivatives of fluorescence signals with respect to temperature for a specific target across multiple runs, in multiple receptacles, and in different locations, within an exemplary thermal module.

100 μL of HCV-2B synthetic target was introduced into five sets of five receptacles, together with 200 μL of oil. Each set the receptacles was then placed into an apparatus configured to perform a thermal melt analysis, which is exemplarily depicted in FIG. 4. The apparatus configured to perform a thermal melt analysis was heated to 90° C. prior to introducing the receptacles. Once introduced to the apparatus, the temperature of the contents of each receptacle was monitored throughout 5 separate melt cycles. Melt temperature averages and standard deviations were calculated by individual receptacle and across all receptacles. The results are summarized in the tables below and FIG. 18. Receptacles are referred to by the abbreviation "R" in the tables below. In the present example the number following the R in the receptacle abbreviation (e.g., R1, R2, R3, R4 or R5) provides information about the physical location of the particular receptacle within the apparatus. As such, each R1, for example, provides temperature information specific to that particular location in the apparatus configured to perform a thermal melt analysis.

TABLE 1

100% Oligo Concentration

|  | Avg. R1 | Avg. R2 | Avg. R3 | Avg. R4 | Avg. R5 |
|---|---|---|---|---|---|
| R Set 1 | 71.46° C. | 71.50° C. | 71.66° C. | 71.58° C. | 71.22° C. |
| R Set 2 | 71.28° C. | 71.78° C. | 71.54° C. | 71.58° C. | 71.00° C. |
| R Set 3 | 71.28° C. | 71.46° C. | 71.60° C. | 71.50° C. | 71.32° C. |
| R Set 4 | 71.28° C. | 71.44° C. | 71.52° C. | 71.46° C. | 71.32° C. |
| R Set 5 | 71.22° C. | 71.68° C. | 71.60° C. | 71.58° C. | 71.08° C. |
| Standard Deviation (SD) | 0.082 | 0.134 | 0.050 | 0.051 | 0.129 |
| MEAN | 71.30° C. | 71.57° C. | 71.58° C. | 71.54° C. | 71.18° C. |
| ACTUAL | 71.71° C. | 71.71° C. | 71.71° C. | 71.71° C. | 71.71° C. |
| Difference | −0.41 | −0.14 | −0.13 | −0.17 | −0.53 |
| 5 Cycle Average (all cycles, receptacles, and locations) |  |  |  |  | 71.43° C. |
| SD |  |  |  |  | 0.19 |

Example 2

Each of a series of four sets of five receptacles was loaded with 100 µL of a different HCV synthetic target, together with 200 µL of oil. Each set of receptacles was then placed into an apparatus configured to perform a thermal melt analysis, which is exemplarily depicted in FIG. 4. The apparatus configured to perform a thermal melt analysis was heated to 90° C. prior to introducing the receptacles. Once introduced to the apparatus, the temperature of the contents of each receptacle was monitored throughout 5 separate melt cycles. Melt temperature averages and standard deviations were calculated by individual receptacle and across all receptacles. The results are summarized in the tables below and FIG. 19. Receptacles are referred to by the abbreviation "R" in the tables below. As in Example 1, the present example the number following the R in the receptacle abbreviation (e.g., R1, R2, R3, R4 or R5) provides information about the physical location of the particular receptacle within the apparatus. As such, each R1, for example, provides temperature information specific to that particular location in the apparatus configured to perform a thermal melt analysis.

TABLE 2

100% Oligo Concentration

| Target Receptacle | HCV-4H; R1 | HCV-3B R2 | HCV-2B R3 | HCV-5A R4 | HCV-1A R5 |
|---|---|---|---|---|---|
| R set 1 | 72.80° C. | 75.00° C. | 71.26° C. | 72.32° C. | 79.04° C. |
| R set 2 | 72.76° C. | 75.10° C. | 71.34° C. | 72.48° C. | 79.00° C. |
| R set 3 | 72.60° C. | 75.00° C. | 71.20° C. | 72.22° C. | 78.86° C. |

TABLE 2-continued

| R set 4 | 72.66° C. | 75.00° C. | 71.30° C. | 72.26° C. | 78.92° C. |
|---|---|---|---|---|---|
| SD | 0.08° C. | 0.04° C. | 0.05° C. | 0.10° C. | 0.07° C. |
| MEAN | 72.70° C. | 75.02° C. | 71.27° C. | 72.32° C. | 78.95° C. |
| ACTUAL | 73.61° C. | 76.42° C. | 71.71° C. | 72.98° C. | 80.2° C. |
| Difference | −0.91 | −1.40 | −0.44 | −0.66 | −1.25 |

|  | R1 | R2 | R3 | R4 | R5 |
|---|---|---|---|---|---|
| 5 Cycle Avg. | 72.70° C. | 75.02° C. | 71.27° C. | 72.32° C. | 78.95° C. |

Example 3

Each of a series of four sets of five receptacles was loaded with 100 µL of a different HCV synthetic target, together with 200 µL of oil. In this example, however, the concentration of each analyte was reduced to 10% of the concentration used in Example 2 above to evaluate sensitivity. Each set of receptacles was then placed into an apparatus configured to perform a thermal melt analysis, which is exemplarily depicted in FIG. 4. The apparatus configured to perform a thermal melt analysis was heated to 90° C. prior to introducing the receptacles. Once introduced to the apparatus, the temperature of the contents of each receptacle was monitored throughout 5 separate melt cycles. Melt temperature averages and standard deviations were calculated by individual receptacle and across all receptacles. The results are summarized in the tables below and FIG. 20. Receptacles are referred to by the abbreviation "R" in the tables below. As in Example 1, the present example the number following the R in the receptacle abbreviation (e.g., R1, R2, R3, R4 or R5) provides information about the physical location of the particular receptacle within the apparatus. As such, each R1, for example, provides temperature information specific to that particular location in the apparatus configured to perform a thermal melt analysis.

TABLE 3

10% Oligo Concentration

| Target Receptacle | HCV-4H R1 | HCV-3B R2 | HCV-2B R3 | HCV-5A R4 | HCV-1A R5 |
|---|---|---|---|---|---|
| R set 1 | 72.94° C. | 74.98° C. | 71.28° C. | 72.34° C. | 78.98° C. |
| R set 2 | 72.96° C. | 75.26° C. | 71.62° C. | 72.76° C. | 79.44° C. |
| R set 3 | 73.10° C. | 75.62° C. | 71.86° C. | 72.92° C. | 79.34° C. |
| R set 4 | 72.58° C. | 75.54° C. | 71.74° C. | 72.64° C. | 78.98° C. |
| MEAN 10% | 72.89° C. | 75.35° C. | 71.62° C. | 72.66° C. | 79.18° C. |
| MEAN 100% | 72.70° C. | 75.02° C. | 71.27° C. | 72.32° C. | 78.95° C. |
| Difference | 0.19 | 0.33 | 0.35 | 0.35 | 0.23 |
| SD 10% | 0.193 | 0.251 | 0.216 | 0.213 | 0.210 |
| SD 100% | 0.08° C. | 0.04° C. | 0.05° C. | 0.10° C. | 0.07° C. |
| Scale Factor | 2.42 | 5.82 | 4.19 | 2.15 | 3.00 |

|  | R1 | R2 | R3 | R4 | R5 |
|---|---|---|---|---|---|
| 5 Cycle Avg. | 72.89 | 75.35 | 71.62 | 72.66 | 79.18 |

While the present invention has been described and shown in considerable detail with reference to certain illustrative embodiments, including various combinations and sub-combinations of features, those skilled in the art will readily appreciate other embodiments and variations and modifications thereof as encompassed within the scope of the present invention. Moreover, the descriptions of such embodiments, combinations, and sub-combinations is not intended to convey that the inventions requires features or combinations of features other than those expressly recited in the claims. Accordingly, the present invention is deemed to include all modifications and variations encompassed within the spirit and scope of the following appended claims.

The invention claimed is:

1. A system for performing a thermal melt analysis, the system comprising:
   a thermal melt analysis module comprising:
      a receptacle holder configured to receive and releasably hold a receptacle;
      a vessel-receiving thermal assembly configured to receive the receptacle and comprising a thermal block assembly for applying thermal energy to the contents of the receptacle;
      a receptacle elevator configured to lower and raise the receptacle holder relative to the vessel-receiving thermal assembly to thereby place the receptacle into the vessel-receiving thermal assembly and to remove the receptacle from the vessel-receiving thermal assembly, respectively; and
      an optical signal detecting device configured to detect optical signals emitted by the contents of a receptacle placed into the vessel-receiving thermal assembly while thermal energy is being applied to the contents by the vessel-receiving thermal assembly; and
   a system controller programmed to control the thermal melt analysis module to perform the thermal melt analysis by:
      directing the receptacle elevator to lower the receptacle holder, thereby placing a receptacle held by the receptacle holder into the vessel-receiving thermal assembly;
      directing the thermal block assembly to apply thermal energy to the contents of the receptacle, such that the thermal block assembly is maintained at a steady-state temperature, wherein the steady-state temperature is greater than ambient temperature; and
      while the thermal block assembly is maintained at the steady-state temperature, directing the optical signal detecting device to measure an optical signal emitted from the contents of the receptacle as the temperature of the contents of the receptacle increases.

2. The system of claim 1, wherein the receptacle holder comprises:
   a cover positioned over a receptacle carried in the receptacle holder; and
   a yoke comprising side walls along opposed sides of the yoke and lateral support flanges extending along bottom edges of the side walls.

3. The system of claim 1, wherein the thermal melt analysis module further comprises a receptacle present detector configured to detect the presence of a receptacle in the receptacle holder.

4. The system of claim 1, wherein the vessel-receiving thermal assembly further comprises a vessel alignment block, wherein the vessel alignment block is configured to position a portion of a receptacle carried by the receptacle holder into the thermal block assembly when the receptacle elevator effects relative movement between the receptacle holder and the vessel-receiving thermal assembly.

5. The system of claim 4, wherein the thermal melt analysis module further comprises a thermal element in thermal contact with the thermal block assembly.

6. The system of claim 5, wherein the thermal element comprises a resistive foil covering at least a portion of the thermal block assembly.

7. The system of claim 4, wherein:
   the vessel alignment block comprises an alignment opening formed therein and configured to hold a receptacle inserted through the opening in a fixed orientation; and
   the thermal block assembly is formed from a thermally conductive material and comprises a receptacle opening formed therein, wherein the thermal block assembly is positioned with respect to the vessel alignment block so that the receptacle opening formed in the thermal block assembly is aligned with the alignment opening formed in the vessel alignment block so that a receptacle inserted through the alignment opening formed in the vessel alignment block is positioned within the receptacle opening formed in the thermal block assembly.

8. The system of claim 4, further comprising at least one signal hole formed in the thermal block assembly and extending into the receptacle opening formed therein, the signal hole being configured to enable the optical signal detecting device to detect optical signals emitted by the contents of a receptacle positioned within the receptacle opening.

9. The system of claim 7, wherein the thermal melt analysis module further comprises an interface block disposed between the vessel alignment block and the thermal block assembly and having an opening aligned with the alignment opening of the vessel alignment block and the receptacle opening of the thermal block assembly.

10. The system of claim 7, wherein the alignment opening formed in the vessel alignment block is circular in cross-section and the receptacle opening formed in the thermal block assembly is circular in cross-section.

11. The system of claim 4, wherein the vessel alignment block comprises a raised center portion extending across a top surface of the vessel alignment block and defining recess shoulder portions on opposite sides of the raised center portion.

12. The system of claim 4, wherein the thermal block assembly comprises one or more receptacle holes formed therein from a top surface of the thermal block assembly and a hollowed-out portion extending from a lower surface of the block and surrounding the one or more receptacle holes without extending into any of the receptacle holes.

13. The system of claim 12, wherein the thermal melt analysis module further comprises a bottom cover secured to a bottom surface of the thermal block assembly to substantially enclose the hollowed-out portion.

14. The system of claim 13, wherein the thermal melt analysis module further comprises signal holes formed in the thermal block assembly and the bottom cover and extending into the receptacle holes formed in the thermal block assembly, the signal holes being configured to enable the optical signal detecting device to detect optical signals emitted by the contents of receptacles positioned within the receptacle holes.

15. The system of claim 4, wherein the vessel alignment block includes one or more mounting blocks raised from a surface thereof at which the vessel alignment block is attached to the thermal block assembly.

16. The system of claim 1, wherein:
   the receptacle holder is configured to receive and releasably hold a plurality of receptacles;
   the vessel-receiving thermal assembly is configured to receive a portion of a plurality of receptacles and to apply thermal energy to the contents of the receptacles; and
   the thermal melt analysis module further comprises a detector translating mechanism configured to move the optical signal detecting device with respect to the vessel-receiving assembly to selectively position a signal detecting channel of the signal detecting device in detecting alignment with two or more different receptacles held within the vessel-receiving thermal assembly.

17. The system of claim 1, wherein the receptacle elevator comprises:
a motor;
a threaded drive screw coupled to an output shaft of the motor; and
a screw follower coupled to the receptacle holder, wherein the drive screw is engaged with the screw follower such that powered rotation of the drive screw by the motor causes translation of the receptacle holder.

18. The system of claim 17, wherein the thermal melt analysis module further comprises:
an encoder coupled to the motor and the threaded drive screw for monitoring a position of the receptacle holder; and
one or more position sensors, each position sensor being configured to detect a predetermined position of the receptacle holder.

19. The system of claim 18, wherein each position sensor comprises a slotted optical sensor configured to be activated by a tab projecting from a portion of the receptacle holder.

20. The system of claim 17, wherein the screw follower is attached to a translating support bracket to which the receptacle holder is attached.

21. The system of claim 20, wherein the thermal melt analysis module further comprises one or more isolation mounts disposed between the translating support bracket and the receptacle holder, each isolation mount comprising:
a pin extending from the translating support bracket though an opening formed in the receptacle holder; and
a coil spring coaxially surrounding the pin.

22. The system of claim 1, wherein the receptacle does not physically contact the thermal block assembly.

23. The system of claim 1, wherein the optical signal detecting device is configured to detect optical signals at two or more distinct and distinguishable wavelengths.

24. The system of claim 23, wherein the optical signal detecting device is configured to detect optical signals at six (6) distinct and distinguishable wavelengths.

25. The system of claim 1, wherein the receptacle holder and the vessel-receiving thermal assembly are configured such that only a lower end of a receptacle held by the receptacle holder can be placed into the vessel-receiving thermal assembly.

26. The system of claim 1, wherein the thermal melt analysis module further comprises a signal detecting device moving mechanism configured to move the optical signal detecting device with respect to vessel-receiving thermal assembly.

27. The system of claim 26, wherein the optical signal detecting device comprises two or more channels, each channel being configured to detect an optical signal at a distinct and distinguishable wavelength, and wherein the signal detecting device moving mechanism is configured to sequentially position each channel relative to the receptacle to enable the signal detecting device to sequentially detect the wavelength corresponding to each channel.

28. The system of claim 26, wherein the signal detecting device moving mechanism comprises:
a motor;
a threaded drive screw coupled to an output shaft of the motor; and
a screw follower coupled to the optical signal detecting device, wherein the drive screw is engaged with the screw follower such that powered rotation of the drive screw by the motor causes translation of the optical signal detecting device.

29. The system of claim 28, wherein the thermal melt analysis module further comprises:
an encoder coupled to the motor and the threaded drive screw for monitoring a position of the optical signal detecting device; and
one or more positions sensors, each position sensor being configured to detect a predetermined position of the optical signal detecting device.

30. The system of claim 29, wherein each position sensor comprises a slotted optical sensor configured to be activated by a tab projecting from a portion of the optical signal detecting device or the signal detecting device moving mechanism.

31. A system for performing a nucleic acid diagnostic assay on a sample carried within a receptacle, comprising:
a target isolation module configured to isolate a target nucleic acid within the sample and to separate the target nucleic acid from non-target components of the sample;
an incubation module configured to incubate the contents of a receptacle and perform an amplification procedure on the separated target nucleic acid within the receptacle;
a thermal melt analysis module configured to receive a receptacle and to apply thermal energy to the contents of the receptacle and to detect and record an optical signal emitted by the contents of the receptacle while thermal energy is being applied to the contents of the receptacle, wherein the thermal melt analysis module includes a thermal block, and wherein thermal energy is applied to the contents of the receptacle by placing a receptacle into operative proximity to the thermal block wherein the thermal melt analysis module is configured to hold the thermal block at a constant elevated temperature relative to ambient temperature for the duration of a thermal melt analysis; and
a receptacle transport mechanism under computer control and configured to:
(1) provide a receptacle containing a sample to the target isolation module,
(2) after the target nucleic acid has been separated from non-target components of the sample, remove the receptacle from the target isolation module;
(3) after removing the receptacle from the target isolation module, provide the receptacle to the incubation module;
(4) after the amplification procedure is complete, remove the receptacle from the incubation module; and
(5) after removing the receptacle from the incubation module, provide the receptacle to the thermal melt analysis module.

* * * * *